United States Patent
Versi et al.

(10) Patent No.: US 10,973,815 B2
(45) Date of Patent: Apr. 13, 2021

(54) DELTA OPIOID AGONIST MU OPIOID ANTAGONIST COMPOSITIONS AND METHODS FOR TREATING PARKINSONS DISEASE

(71) Applicant: VERSI GROUP, LLC, Gladstone, NJ (US)

(72) Inventors: Ebrahim Versi, Gladstone, NJ (US); Bruce Reidenberg, Rye, NY (US)

(73) Assignee: VERSI GROUP, LLC, Gladstone, NJ (US)

( * ) Notice: Subject to any disclaimer, the term of this patent is extended or adjusted under 35 U.S.C. 154(b) by 0 days.

(21) Appl. No.: 16/077,575

(22) PCT Filed: Mar. 30, 2017

(86) PCT No.: PCT/US2017/024989
§ 371 (c)(1),
(2) Date: Aug. 13, 2018

(87) PCT Pub. No.: WO2017/173067
PCT Pub. Date: Oct. 5, 2017

(65) Prior Publication Data
US 2019/0038620 A1 Feb. 7, 2019

Related U.S. Application Data

(60) Provisional application No. 62/315,717, filed on Mar. 31, 2016.

(51) Int. Cl.
*A61K 31/495* (2006.01)
*A61P 25/14* (2006.01)
*A61P 25/16* (2006.01)

(52) U.S. Cl.
CPC ............ *A61K 31/495* (2013.01); *A61P 25/14* (2018.01); *A61P 25/16* (2018.01)

(58) Field of Classification Search
CPC combination set(s) only.
See application file for complete search history.

(56) References Cited

U.S. PATENT DOCUMENTS

| 6,875,772 B2 | 4/2005 | Neustadt et al. |
| 7,030,124 B2 | 4/2006 | Chang et al. |

(Continued)

FOREIGN PATENT DOCUMENTS

| WO | WO2005053703 A1 | 6/2005 |
| WO | WO 2007/027987 | * 3/2007 |

OTHER PUBLICATIONS

Padovan-Neto et al. Nitric oxide synthase inhibition attenuates L-dopa-induced dyskinesias in a rodent model of Parkinson's disease. Neuroscience, 159, 2009, 927-935.*

(Continued)

*Primary Examiner* — Anna Pagonakis
(74) *Attorney, Agent, or Firm* — Marianne Fuierer; Olive Law Group, PLLC

(57) ABSTRACT

The present invention provides for compositions and methods for the treatment of Parkinson's disease comprising a compound of formula (i):

(Continued)

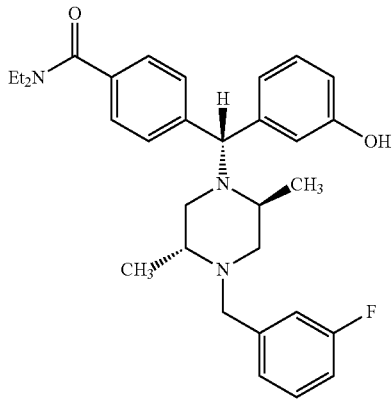

or a pharmaceutically effective salt or ester thereof alone or in combination with L-DOPA to provide a synergistic effect, thereby providing methods of (1) treating patients with Parkinson's Disease for whom L-DOPA is no longer effective, (2) treating patients with Parkinson's Disease who developed dyskinesia due to L-DOPA, (3) treating patients with Parkinson's Disease who have are receiving deep brain stimulation and (4) treating patients with Parkinson's Disease whose symptoms interfere with activities of daily living.

5 Claims, 27 Drawing Sheets

(56) References Cited

U.S. PATENT DOCUMENTS

| | | | |
|---|---|---|---|
| 7,253,173 B2 | 8/2007 | Brown et al. | |
| 7,727,993 B2 | 6/2010 | Kase et al. | |
| 8,642,599 B2 * | 2/2014 | Chang | A61K 31/495 514/252.12 |
| 9,289,423 B2 * | 3/2016 | Mouradian | A61K 31/485 |
| 2002/0052007 A1 | 5/2002 | Chang et al. | |
| 2002/0137669 A1 | 9/2002 | Brotchie | |
| 2010/0260737 A1 | 10/2010 | Tarozzi et al. | |
| 2014/0315922 A1 | 10/2014 | Chang et al. | |
| 2016/0200689 A1 | 7/2016 | Chang et al. | |

OTHER PUBLICATIONS

Chou-Talalay et al. (Advances in Enzyme Regulation, 22, 1985).*
Benabid. Deep brain stimulation for Parkinsons' disease. Current Opinion in Neurobiology, 2003, 13: 696-706.*
Broom, D.C. et al. "Nonpeptidic delta-opioid receptor agonists reduce immobility in the forced swim assay in rats", Neuropsychopharmacology, 2002, 26(6):744-755.
Chang, K.J. et al. "A novel, potent and selective nonpeptidic delta opioid receptor agonist BW373U86", J Pharmacol Exp Ther, 1993, 267(2):852-857.

Comer, S.D. et al. "Convulsive effects of systemic administration of the delta opioid agonist BW373U86 in mice", J Pharmacol Exp Ther, 1993, 267(2):888-895.
Cox, H. et al. "The selective kappa-opioid receptor agonist U50, 488 reduces L-dopa-induced dyskinesias but worsens parkinsonism in MPTP-treated primates", Experimental Neurology, 2007, vol. 205, pp. 101-107.
Cuello, C.A. et al. "Evidence for a long leu-enkephalin striopallidal pathway in rat brain", Nature, 1978, 271:178-180.
De Ceballos, M.L. et al. "Parallel alterations in Met-enkephalin and substance P levels in medial globus pallidus in Parkinson's disease patients", Neurosci. Lett., 1993, 160:163-166.
Gerfen, C.R. et al. "Distribution of striatonigral and striatopallidal peptidergic neurons in both patch and matrix compartments: An in situ hybridization histochemistry and fluorescent retrograde tracing study", Brain Res., 1988, 460:161-167.
Henry, B. et al. "Potential of opioid antagonists in the treatment of levodopa-induced dyskinesias in Parkinson's disease", Drugs Aging, 1996, 9:149-158.
Henry, B. et al. "Mu-and delta-opioid receptor antagonist reduce levodopa-induced dyskinesia in the MPTP-lesioned primate model of Parkinson's disease", Experimental Neurology, 2011, 171:139-146.
Herrero, M.T. et al. "Effects of L-DOPA on preproenkephalin and preprotachykinin gene expression in MPTP-treated monkey striatum", Neurosci., 1995, 68:1189-1198.
Hill, M.P. et al. "δ-opioid receptor agonists as a therapeutic approach in Parkinson's disease", Drugs News Perspect., 2000, 13(5):261-268.
Hille, C.J, et al. "Antiparkinsonian action of a δ opioid agonist in rodent and primate models of Parkinson's disease", Exp. Neurol., 2001, 172:189-198.
Johnston, T.H. et al. "DPI-289, a novel bi-functional delta agonist /my antagonist (DAMA) therapy for Parkinson's disease", 18th International congress of Parkinson's disease and movement disorders, Stockholm, Sweden, Jun. 8-12, 2014.
Jolkkonen, J. et al. "L-DOPA reverses altered gene expression of substance P but not enkephalin in the caudate-putamen of common marmosets treated with MPTP", Brain Res. Mol. Brain Res., 1995, 32:297-307.
Maneuf, Y.P. et al. On the role of enkephalin cotransmission in the GABAergic striatal efferents to the globus pallidus. Exp. Neurol., 1994, 125:65-71.
Negus, S.S. et al. "Behavioral effects of the systemically active delta opioid agonist BW373U86 in rhesus monkeys", J. Pharmacol. Exp. Ther., 1994, 270, 1025-34.
Negus, S.S. et al. "Role of delta opioid receptors in the reinforcing and discriminative stimulus effects of cocaine in rhesus monkeys", J. Pharmacol. Exp. Ther., 1995, 273: 1245-56.
Negus, S.S. et al. "Behavioral effects of the delta-selective opioid agonist SNC80 and related compounds in rhesus monkeys", J. Pharmacol. Exp. Ther., 1998, 286: 362-75.
Nisbet, A.P. et al. "Perproenkephalin and preprotachykinin messenger RNA expression in normal human basal ganglia and in Parkinson's disease", Neurosci. 1995, 66:361-376.
Silverdale, M.A. et al. "Potential nondopaminergic drugs for Parkinson's disease", Parkinson's Disease: Advances in Neurology, 2003, 91:273-291.
Cassano, P. et al. "Pramipexole in Treatment-Resistant Depression: An Extended Follow-Up", Depression and Anxiety, 2004, vol. 20, pp. 131-138.

* cited by examiner

MPTP-lesioned macaques with established motor complications

Activity time-course

L-DOPA naïve MPTP-lesioned macaques

Parkinsonian disability time-course

MPTP-lesioned macaques with established motor complications

Parkinsonian disability time-course

L-DOPA naïve MPTP-lesioned macaques

Bradykinesia time-course

MPTP-lesioned macaques with established motor complications

Bradykinesia time-course

L-DOPA naïve MPTP-lesioned macaques

Range of movement time-course

MPTP-lesioned macaques with established motor complications

Range of movement time-course

L-DOPA naïve MPTP-lesioned macaques

Postural impairment time-course 0-3 hour totals 3-6 hour totals

MPTP-lesioned macaques with established motor complications

Postural impairment time-course 0-3 hour totals 3-6 hour totals

L-DOPA naïve MPTP-lesioned macaques

Alertness time-course

L-DOPA naïve MPTP-lesioned macaques

Dyskinesia time-course

Postural instability time-course

Alertness time-course

Range of movement

| L-DOPA | DPI-289 | vehicle-vehicle cf. (h) | | | | | |
|---|---|---|---|---|---|---|---|
| | | 1 | 2 | 3 | 4 | 5 | 6 |
| LDl | vehicle | * | ns | ns | ns | ns | ns |
| LDl | 20 mg/kg | * | ns | ns | ns | ns | ns |
| LDh | vehicle | *** | ns | ns | ns | ns | ns |

Bradykinesia time-course

Figure 27 A
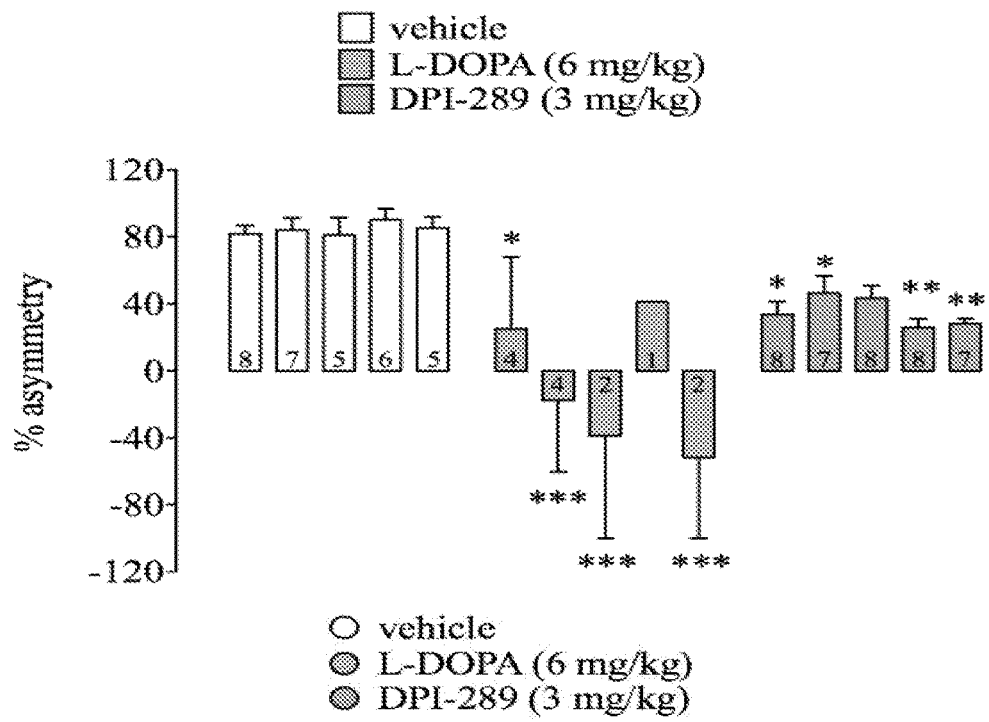
Figure 27 B
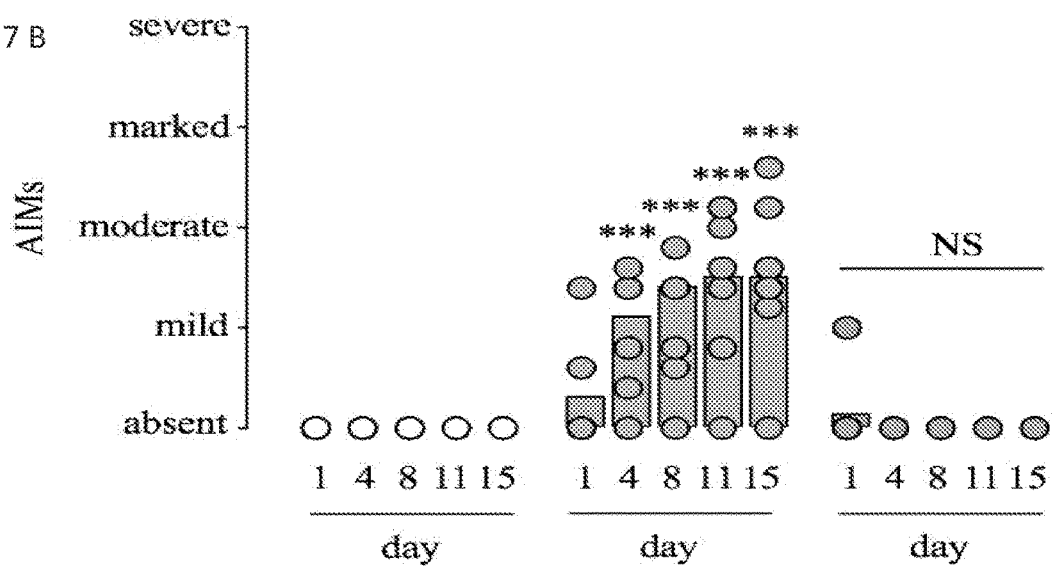
Figure 27

DELTA OPIOID AGONIST MU OPIOID ANTAGONIST COMPOSITIONS AND METHODS FOR TREATING PARKINSONS DISEASE

CROSS-REFERENCE TO RELATED APPLICATIONS

This application is filed under the provisions of 35 U.S.C. § 371 and claims the priority of International Patent Application No. PCT/US2017/024989 filed on Mar. 30, 2017 which in turn claims priority to U.S. Provisional Patent Application No. 62/315,717 filed on Mar. 31, 2016, the contents of which is hereby incorporated by reference herein for all purposes.

BACKGROUND OF THE INVENTION

Field of the Invention

The present invention relates to compositions and methods of treatment for Parkinson's disease, by administration to a subject suffering or susceptible to same, a diarylmethylpiperazine compound that exhibits both delta opioid receptor agonist and mu opioid receptor antagonist activity and optionally in combination with other active Parkinson treating agents.

Description of the Related Art

Parkinson's disease is a degenerative disorder identified by the loss of motor control progressing to loss of motor functions as well as Parkinsonian dementia in many cases. The pathophysiology of the disease is dominated by a loss of dopamine containing neurons in the brain, particularly in the basal ganglia areas.

Current medical therapy for Parkinson's disease is based primarily around the replacement of the dopamine deficit through the administration of L-DOPA with or without other dopamine agonists. However, after 3-5 years of L-DOPA treatment alone patients develop motor fluctuations due to "wearing-off" of the therapeutic effect, "on-off" fluctuations in efficacy immediately after dosing, or most commonly, an "overshoot" of effect manifested as abnormal involuntary movements (AIMs; dyskinesias) (Hill et al., 2000; Silverdale et al., 2003). The coadministration of dopamine agonists (primarily ergot-derived) with L-DOPA slows the development of these side-effects but does not prevent their eventual onset (Hill et al., 2000; Silverdale et al., 2003). Critically, once patients have experienced L-DOPA-induced dyskinesias they are "primed" for dyskinesias in response to any currently available dopamine-based therapeutic (Hill et al., 2000). In light of these debilitating side-effects and the loss of efficacy over extended L-DOPA use, non-dopaminergic therapy for Parkinson's disease would be highly desirable, whether as a monotherapy or as an adjunct therapy to low-dose L-DOPA administration.

Some anti-parkinsonian effect has been demonstrated for delta receptor activation by rodent and primate studies with the delta receptor-selective agonist, SNC80 (Hille et al, 2001). SNC80 is a highly selective delta receptor agonist and is an analogue of benzhydrylpiperazines such as BW373U86 (Chang et al., 1993). SNC80 at 10 mg/kg i.p. restored behavioral deficits observed in rats treated with reserpine or dopamine receptor antagonists (haloperidol or SCH23390) including ambulatory behavior, grooming, rearing, social interaction and exploration, and static investigation. When administered at similar dose levels to MPTP-treated marmosets, SNC80 restored motor activity, bradykinesia and disability scores to normal. The parkinsonian posture induced by MPTP treatment in this model was not statistically reversed by SNC80 although substantial improvements were observed in some individual animals (Hille et al., 2001).

These reports, in both rodent and non-human primate models of Parkinson's disease, indicate that the delta opioid receptor agonist SNC80 has a powerful anti-parkinsonian effect. Interestingly, even at relatively high doses behavior returned to normal levels but did not show the hyperkinesias associated with supra-optimal doses of L-DOPA (Hille et al, 2001). The mechanism of action appears to be via the delta receptor (Hille et al, 2001). However, SNC80 is neither orally active nor particularly safe for use in a clinical setting. SNC80 has been shown to produce seizure-like convulsions in mice and rats, and as such cannot be pursued for clinical study (Broom, et al., 2002).

A highly selective mu antagonist cyprodime was shown to reduce completely L-DOPA-induced dyskinesia in the MPTP-lesioned primate (marmosets) model of Parkinson's disease without attenuation of the anti-parkinsonian actions of L-DOPA (Henry et al., 2001). It appears that the highly selective mu antagonist cyprodime was more effective than less selective antagonists such as naltrexone and naltrindole at the dose of 10 mg/kg i.p. This data plus the demonstrated increase in the synthesis of proenkephalin A and B in basal ganglia in the animal model of L-DOPA-induced dyskinesia and in postmortem tissue from Parkinson's disease patients treated with conventional therapy (Nisbet et al., 1995; Maneuf et al., 1994; De Ceballos et al., 1993) provides strong evidence that mu-receptor activation may contribute to the development of dyskinesia in Parkinson's disease patients after chronic L-DOPA based therapy.

Consequently, it follows that treatment a compound with dual opioid action of delta receptor agonism and mu receptor antagonism would not only have anti-Parkinsonian effects but also would reduce or eliminate the potential of delta receptor agonist induced dyskinesia. Further such mu antagonism may also reduce L-DOPA induced dyskinesia.

Thus, there is a need for an effective opioid-based treatment for Parkinson's disease that not only acts as a delta opioid receptor agonist but also exhibits mu opioid receptor antagonist activity and has the ability to overcome the negative side effects of L-DOPA used in the treatment of Parkinson's disease.

SUMMARY OF THE INVENTION

L-DOPA therapy is the gold standard for treating Parkinson's disease. Unfortunately, the value of current L-DOPA based therapies for Parkinson's disease is limited by significant complications of long-term treatment, particularly dyskinesia. The present invention provides for a novel therapy, with the ability, as monotherapy, to alleviate or reduce parkinsonian symptoms to the same extent as currently-available dopamine replacing agents, while producing fewer side effects. Additionally, the present invention provides for a compound that exhibits delta opioid receptor agonist and mu opioid antagonist activity in combination with low-doses of an existing dopaminergic such as L-DOPA that produces an equivalent anti-parkinsonian response comparable to higher, optimal doses of L-DOPA, but with fewer negative side-effects. The present invention relates to a composition and a method of treating Parkinson's disease comprising administering to said subject an effective amount of a therapeutic composition comprising a compound that exhibits delta opioid receptor agonist and mu opioid antagonist activity, optionally in combination with other active Parkinson treating agents. Preferably, the compound is a diarylmethylpiperazine compound, wherein the compound has the structure of formula (i) (DPI-289), as shown below:

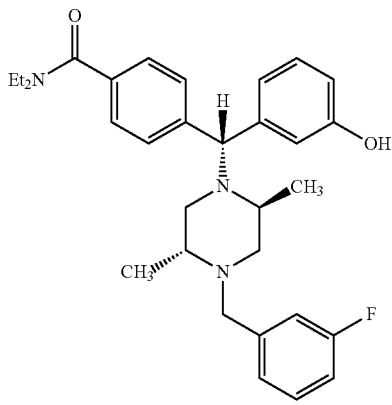

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt or ester thereof.

In another aspect, the diarylmethylpiperazine compound having the above structure of Formula (i) may be administered in combination with other Parkinson's treating agents such as dopamine agonists, including but not limited to apomorphine, bromocriptine, cabergoline, ciladopa, dihydrexidine, dinapsoline, doxanthrine, epicriptine, lisuride, piribedil, pramipexole propylnorapomorphine, quinagolide, ropinirole, rotigotine, roxindole, sumanirole, benztropine mesylate, entacapone, selegiline hydrochloride, carbidopa, pergolide, amantadine hydrochloride and tolcapone. Dopamine agonists rarely cause dyskinesia such as induced by L-DOPA but they have poor efficacy and thus combining them with DPI-289 can provided increase efficacy and cause a synergistic effectiveness.

In yet another aspect, the present invention relates to a method of treating Parkinson's disease in subject that cannot take L-DOPA because of the negative side effects, wherein administration of the structure of formula (i) (DPI-289) as shown below:

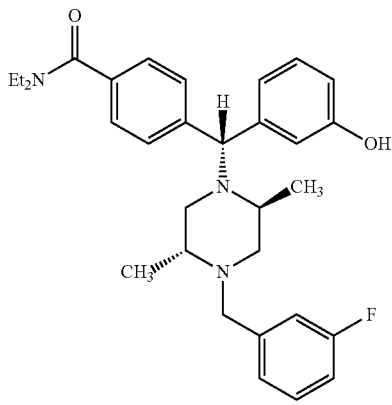

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt, in a therapeutically effective amount having the effectiveness to delay or eliminate the need for deep brain stimulation in a subject suffering from Parkinson's disease.

In a still further aspect, the present invention provide for a treatment for a subject who is L-DOPA experienced and having dyskinesia adverse events including over-activity of movement, dyskinesia, reduced "ON-time," postural instability and/or reduced alertness, wherein the treatment comprises administering a therapeutically effective amount of formula (i):

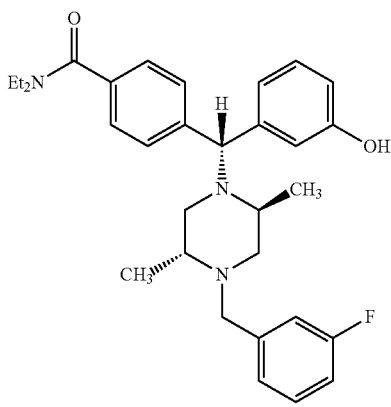

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt or ester thereof.

In another aspect, the present invention provides for treatment of a subject who has developed L-DOPA induced dyskinesia or unable to tolerate L-DOPA, the method comprising the administration of formula (i) (DPI-289) in a single dose amount ranging from about 1 mg/kg to about 100 mg/kg, preferably 5 to 20 mg/kg, administered orally several times a day to increase improvement of movement and improvement in self-care including feeding, dressing, personal hygiene without causing dyskinesia. The daily dose of DPI-289 would be about 5 mg/kg to about 500 mg/kg, preferably 25 mg/kg to 100 mg/kg.

In yet another aspect, the present invention provides for a composition comprising a synergistic combination comprising a low dose of L-DOPA, that being, from about 1 to 10 mg/kg of L-DOPA per day, is combined with formula (i) (DPI-289) in an amount from about 1 mg/kg to 100 mg/kg, preferably 5 mg/kg to 20 mg/kg, where said combination causes a synergistic effect that provides for extended reduction in parkinsonian symptoms relative to either components alone or a higher dose of L-DOPA alone (about 10 mg/kg to 100 mg/kg). The synergistic combination provides for Enhancement of the efficacy of sub-therapeutic doses of L-DOPA Enhancement of the efficacy of sub-therapeutic doses of L-DOPA without causing dyskinesia Enhancement of the efficacy of L-DOPA in patients who have become less responsive to previously optimally response to L-DOPA Enhancement of the efficacy of L-DOPA in patients who have become less responsive to previously optimally response to L-DOPA without causing dyskinesia Enhancement of "ON" time meaning L-DOPA is effective for a longer period with limited reduction in symptomatic "on and off" fluctuations Maintenance of efficacy of L-DOPA despite the need to reduce L-DOPA doses to limit dyskinesia Prevention or reduction of L-DOPA induced dyskinesia Prevention or reduction of L-DOPA induced dyskinesia without reduction of the efficacy of L-DOPA In yet another aspect, the present invention provides for a composition comprising a synergistic effect of formula (i) DPI-289 such that the duration of action of a single low dose of L-DOPA (about 1 to 10 mg/kg) is prolonged. The dose of formula (i) (DPI-289) in an amount from about 1 mg/kg to 25 mg/kg, preferably 2 mg/kg to 5 mg/kg, where said combination causes a synergistic effect that provides for prolonged reduction in parkinsonian symptoms. The synergistic combination provides for Prolongation of the duration of effect of sub-therapeutic doses of L-DOPA and the combination lasts longer than that of the high dose (optimal) of L-DOPA Prolongation of the effect of DPI-289 with concomitant use of L-DOPA As used herein, the term "a synergistic effect" is present when the activity of the active compounds in a combination exceeds the total of the action of the active compounds when applied individually.

A therapeutic composition of the present invention comprising a synergistic combination comprising formula (i) (DPI-289) and a low dose of L-DOPA may be administered by any suitable administrative mode, e.g., an administration modality selected from the group consisting of oral, rectal, topical, sub-lingual, mucosal, nasal, ophthalmic, subcutaneous, intramuscular, intravenous, transdermal, spinal, intrathecal, intracranial, intra-articular, intra-arterial, sub-arachnoid, bronchial, lymphatic, vaginal and intra-uterine administration.

The synergistic composition may comprise formula (i) (DPI-289) in a single dose amount from about 1 mg/kg to about 100 mg/kg, and more preferably, from about 5 mg/kg to about 20 mg/kg. L-DOPA is included in an amount that does not cause negative side effects such as dyskinesia, postural instability and/or reduced alertness. Preferably a daily low dose ranges from about 100 mg to 1000 mg a day. Higher doses of L-DOPA can ranged from 2000 to 6000 mg per day. However, such higher doses can present negative effects, and as such, reducing the amount to a lower dose in combination with formula (i) provides for effective treatment of PD without negative effects caused by higher doses of L-DOPA.

Another aspect of the present invention relates to use of a synergistic combination comprising Formula (i) in combination with a low dose of L-DOPA in the manufacture of a medicament or pharmaceutical for the treatment of Parkinson's disease.

Various other aspects, features and embodiments of the invention will be more fully apparent from the ensuing disclosure and appended claims.

BRIEF DESCRIPTION OF THE FIGURES

FIG. 1A shows time course data as mean±s.e.m. (FIG. 1A; time-course) or cumulated shown in FIG. 1B for 0-3 h; or FIG. 1C for 3-6 hr. N=8 for all treatment groups. *//* represents P<0.05, P<0.01 or P<0.001 cf. vehicle-treatment; 2-way RM ANOVA (FIG. 1A) or 1-way RM-ANOVA with Holm-Sidak's Multiple Comparison test (FIGS. 1B and C) (ns—not significant).

(FIG. 2A shows time-course) or cumulated shown in FIG. 2B for 0-3 h; or FIG. 2C for 3-6 hr. N=8 for all treatment groups. *//* represents P<0.05, P<0.01 or P<0.001 cf vehicle-treatment; 2-way RM ANOVA (FIG. 2A) or 1-way RM-ANOVA with Holm-Sidak's Multiple Comparison test (FIGS. 2B and C). *//* represents P<0.05, P<0.01 or P<0.001 cf.

(FIG. 6A shows time-course) or cumulated for 0-3 h shown in FIG. 6B, or shown for 3-6 h in FIG. 6C. N=8 for all treatment groups. *//* represents P<0.05, P<0.01 or P<0.001 cf. vehicle-treatment; 2-way RM ANOVA (FIG. 6A) or 1-way RM-ANOVA with Holm-Sidak's Multiple Comparison test (FIGS. 6 B and C).

(FIG. 8A shows time-course) or cumulated for 0-3 h shown in FIG. 8B or 3-6 h shown in FIG. 8C. N=8 for all treatment groups. *** represents P<0.001 cf. vehicle-treatment; 2-way RM ANOVA (FIG. 8A) or 1-way RM-ANOVA with Holm-Sidak's Multiple Comparison test (FIGS. 8B and 8C).

(FIG. 10A shows time-course) or cumulated 0-3 h shown in FIG. 10B or for 3-6 h shown in FIG. 10C. N=8 for all treatment groups. */**represents P<0.05 or P<0.01 cf. vehicle-treatment; 2-way RM ANOVA (FIG. 10A) or 1-way RM-ANOVA with Holm-Sidak's Multiple Comparison test (FIGS. 10B and C).

(FIG. 12A shows time-course) or cumulated for 0-3 h shown in FIG. 12B or for 3-6 h shown in FIG. 12C. N=8 for all treatment groups. *//* represents P<0.05, P<0.01 or P<0.001 cf. vehicle-treatment; 2-way RM ANOVA (FIG. 12A) or 1-way RM-ANOVA with Holm-Sidak's Multiple Comparison test (FIGS. 12B and C).

(FIG. 14A shows time-course) or cumulated for 0-3 h shown in FIG. 14B or for 3-6 h shown in FIG. 14C. N=8 for all treatment groups. *//* represents P<0.05, P<0.01 or P<0.001 cf. vehicle-treatment; 2-way RM ANOVA (FIG. 14A) or 1-way RM-ANOVA with Holm-Sidak's Multiple Comparison test (FIGS. 14B and C).

(FIG. 16A shows time-course) or cumulated for 0-3 h shown in FIG. 16B or for 3-6 h shown in FIG. 16C. N=8 for all treatment groups. 2-way RM ANOVA (FIG. 16A) or 1-way RM-ANOVA with Holm-Sidak's Multiple Comparison test (FIG. 16B and FIG. 16C).

(FIG. 17A shows time-course) or cumulated for 0-6 h shown in FIG. 17B. N=8 for all treatment groups. 2-way RM ANOVA (FIG. 17A) or 1-way RM-ANOVA with Holm-Sidak's Multiple Comparison test (FIG. 17B).

(FIG. 18A shows time-course) or cumulated for 0-6 h shown in FIG. 18B. N=8 for all treatment groups. 2-way RM ANOVA (FIG. 18A) or Friedman's test with Dunn's post-hoc (FIG. 18B).

(FIG. 19A shows time-course) or cumulated for 0-6 h shown in FIG. 19B. N=8 for all treatment groups. 2-way RM ANOVA (FIG. 19A) or Friedman's test with Dunn's post-hoc (FIG. 19B).

(FIG. 20A shows time-course) or cumulated for 0-6 h shown in FIG. 20B. N=8 for all treatment groups. 2-way RM ANOVA (FIG. 20A) or Friedman's test with Dunn's post-hoc (FIG. 20B).

(FIG. 21A shows time-course) or cumulated for 0-6 h shown in FIG. 21B. N=8 for all treatment groups. 2-way RM ANOVA (FIG. 21A) or Friedman's test with Dunn's post-hoc (FIG. 21B).

(FIG. 22A shows time-course) or cumulated for 0-6 h shown in FIG. 22B. N=8 for all treatment groups. 2-way RM ANOVA (FIG. 22A) or Friedman's test with Dunn's post-hoc (FIG. 22B).

(FIG. 23A shows time-course) or cumulated for 0-6 h shown in FIG. 23B. N=8 for all treatment groups. 2-way RM ANOVA (FIG. 23A) or Friedman's test with Dunn's post-hoc (FIG. 23B).

FIG. 24B shows the total ON-time, FIG. 24 shows the Good ON-time and FIG. 24C shows the BAD ON-time.

FIG. 27A shows reduction in postural asymmetry of unilateral 6-OHDA-lesioned Rats by DPI-289 or L-DOPA. FIG. 27B shows the absence of dyskinesia following repeated administration of DPI-289 to unilateral 6-OHDA-lesioned Rats. N=8 rats per group. Statistical significance was assessed by a two-way ANOVA and Holm-Sidak's multiple comparisons test.

DETAILED DESCRIPTION OF THE INVENTION

Figure 1:
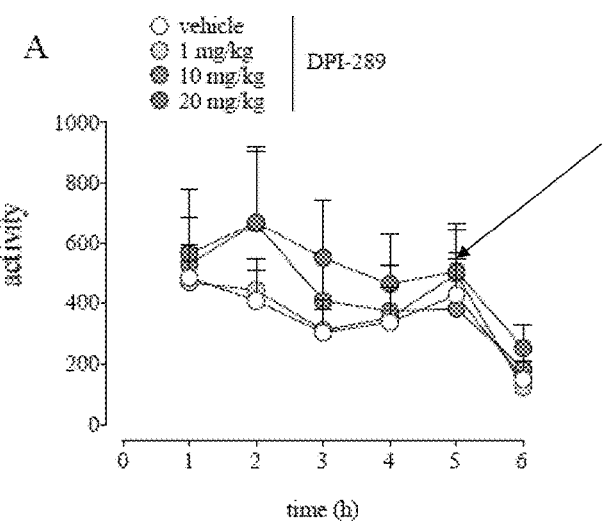
FIG. 1 shows effect of Formula (i) (DPI-289) on movement activity in L-DOPA naïve MPTP-lesioned primates. This activity is measured by an infra-red movement detector and captures all movement, normal and abnormal. MPTP-lesioned cynomolgus monkeys received acute oral administration of either vehicle or Formula (i) (1, 10 or 20 mg/kg) according to a randomized incomplete Latin Square-type. Levels of activity were assessed every minute over the entire 6 h observation.
Figure 1:
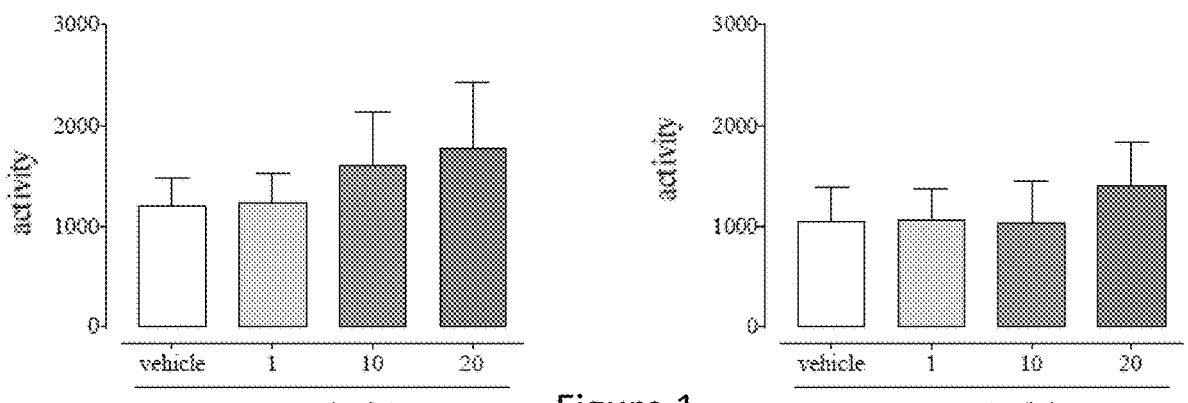

In one broad method aspect of the present invention, a diarylmethylpiperazine compound that exhibits delta opioid receptor agonist activity and also mu opioid receptor antagonist activity as hereinafter more fully described is administered to a subject in need of treatment for Parkinson's disease.

The invention broadly contemplates the treatment of Parkinson's disease by using a monotherapy treatment, involving compounds of the invention as singular therapeutic agents in administered therapeutic compositions, or co-therapy treatment, wherein a compound in accordance with the present invention is administered contemporaneously, e.g., simultaneously, or sequentially, with another therapeutic Parkinson agent.

In a particularly preferred method aspect of the invention, Parkinson's disease is treated by administering to a subject in need of such treatment an effective amount of a compound of Formula (i) (DPI-289) or a pharmaceutically acceptable ester or salt thereof.

Examples of pharmaceutically acceptable esters of compounds of formula (i) include carboxylic acid esters of the hydroxyl group in the compounds of Formula (i) (DPI-289) where OH on any of the rings in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate). However, esters that are not pharmaceutically acceptable may also find use, for example, in the preparation or purification of a pharmaceutically acceptable compound. All salts, whether or not derived from a pharmaceutically acceptable acidic moiety, are within the scope of the present invention.

Examples of pharmaceutically acceptable salts of the compounds of Formula (i) include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4{}^+$, or $NR'_4{}^+$ (wherein R' is for example a $C_{1-4}$ alkyl group).

For therapeutic use, salts of the compound of Formula (i) will be pharmaceutically acceptable, i.e., they will be salts derived from a pharmaceutically acceptable acid or base. However, salts of acids or bases that are not pharmaceutically acceptable may also find use, for example, in the preparation or purification of a pharmaceutically acceptable compound. All esters, whether or not derived from a pharmaceutically acceptable acid or base, are within the scope of the present invention.

The present invention also contemplates pharmaceutical formulations, both for veterinary and for human medical use, which comprise as the active agent one or more compound(s) of the invention.

In such pharmaceutical formulations, the diarylmethylpiperazine compound preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, optic, ophthalmic, subcutaneous, intramuscular, intravenous, transdermal, spinal, intrathecal, intracranial, intra-articular, intra-arterial, sub-arachnoid, bronchial, lymphatic, vaginal and intra-uterine administration.

When the active agent of the present invention is utilized in a formulation comprising a liquid solution, the formulation advantageously may be administered parenterally. When the active Parkinson agent of the present invention is employed in a liquid suspension formulation or as a powder in a biocompatible carrier formulation, the formulation may be advantageously administered orally, rectally, or bronchially.

When the active Parkinson agent of the present invention is utilized directly in the form of a powdered solid, the active agent may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

In some applications, it may be advantageous to utilize the active Parkinson agent of the present invention in a "vectorized" form, such as by encapsulation of the active agent in a liposome or other encapsulant medium, or by fixation of the active Parkinson agent of the present invention, e.g., by covalent bonding, chelation, or associative coordination, on a suitable biomolecule, such as those selected from proteins, lipoproteins, glycoproteins, and polysaccharides.

The formulations comprising the active Parkinson agent of the present invention may conveniently be presented in unit dosage forms and may be prepared by any of the methods well known in the art of pharmacy. Such methods generally include the step of bringing the active Parkinson compound(s) of the present invention into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active Parkinson agent of the present invention to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active Parkinson agent of the present invention with preservative agents and isotonic agents. Such formulations are preferably adjusted to a pH and isotonic state compatible with the nasal mucous membranes.

Formulations for rectal or vaginal administration may be presented as a suppository or pessary with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active Parkinson agent of the present invention dissolved or suspended in one or more media, such as mineral oil, petroleum, polyhydroxy alcohols, or other bases used for topical pharmaceutical formulations.

The compounds of the invention may also be delivered through the skin or muscosal tissue using conventional transdermal drug delivery systems, i.e., transdermal "patches" wherein a composition of the present invention is typically contained within a laminated structure that serves as a drug delivery device to be affixed to the body surface. In such a structure, the pharmaceutical composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the active agent-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

Transdermal formulations may be prepared by incorporating the active Parkinson agent of the present invention in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. The transdermal formulation would optimally be comprised of a backing, a reservoir layer containing the composition, and an adhesive. The transdermal system would be optimized to allow prolonged wear (up to 7 days) and consistent composition delivery through the skin. The excipients necessary in the transdermal system would support composition stability. The adhesive would be permeable to the compound and to water to avoid occlusion damage to the skin. The backing layer would also be permeable to water vapor, but not wettable, to both avoid occlusion damage to the skin and to support prolonged wear.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

Depending on the specific condition to be treated, animal subjects may be administered compounds of the present invention at any suitable therapeutically effective and safe dosage, as may readily be determined within the skill of the art, and without undue experimentation.

In general, while the effective dosage of Formula (i) (DPI-289) of the invention for therapeutic use may be widely varied in the broad practice of the invention, depending on the specific condition involved, the delivery modes that being either oral, transdermal or other modes, the stage of the individual's disease and the duration and dosage of the individual's prior exposure to L-DOPA as readily determinable within the skill of the art, suitable therapeutic doses of the compounds of the invention, for each of the appertaining compositions described herein, and for achievement of therapeutic benefit in treatment of each of the conditions described herein, will be in the range of or approximately 50 micrograms (μg) to 500 milligrams (mg) per kilogram body weight of the recipient per day, preferably in sub doses. The desired oral dose may be presented as one, two, three, four, five, six, or more sub-doses administered at appropriate intervals throughout the day.

The mode of administration and dosage forms will of course affect the therapeutic amounts of the Parkinson agent of the present invention which are desirable and efficacious for the given treatment application.

In oral administration, dosage levels for compounds of the present invention may be on the order of 1-100 mg/kg body weight/day preferably 5-25 mg/kg body weight/day. In tablet dosage forms, typical active agent dose levels are on the order of 100-1000 mg per tablet.

The following examples are illustrative of synthetic procedures that may be advantageously utilized to synthesize the compound of the present invention.

Example 1 (Formula (i) (DPI-289)

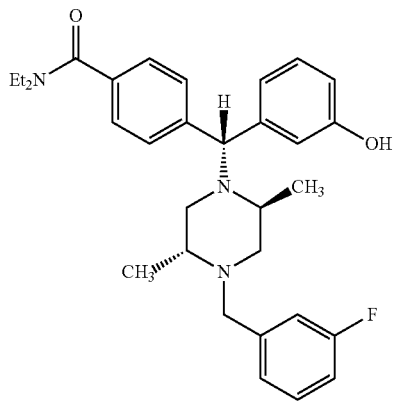

4-((alpha-R)-alpha-((2S,5R)-2,5-Dimethyl-4-(3-fluorobenzyl)-1-piperazinyl)-3-hydroxybenzyl)-N,N-diethylbenzamide Method A—Alkylation with Phenol Protection A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into water (2000 mL) and the layers separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates combined and the solvent removed under reduced pressure to give 3-(bromophenoxy)-tert-butyldimethylsilane (669 g, 98.4%) as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture of 3-bromophenoxy-tert-butyldimethylsilane (27.3 g, 92.6 mmol) and dibromoethane (3.45 g, 18.4 mmol) in inhibitor-free anhydrous tetrahydrofuran (100 mL) to a solution of magnesium turnings (3.57 g, 147 mmol) in inhibitor-free anhydrous tetrahydrofuran (200 mL) at reflux. After stirring for one hour at reflux the light brown clear mixture was cooled to room temperature.

4-Carboxybenzaldehyde (100.3 g, 0.67 mol) was dissolved/suspended in toluene (1200 mL), dimethylformamide (0.15 mL) was added and the suspension was stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water (2×300 mL), dilute sodium carbonate solution (saturated Na$_2$CO$_3$:H$_2$O, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil (115.7 g, 84%) which was used without further purification.

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Division of Dowpharma, The Dow Chemical Company, Cambridge, England) with toluene (400 mL). The reaction mixture was heated to reflux under nitrogen until no additional water was observed in the trap (ca. 2 hours). The reaction mixture was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of saturated aqueous ammonium chloride (20 mL). Anhydrous magnesium sulfate (20 g) was added and the reaction was filtered. Solvent was removed under vacuum and the residue was redissolved in ethyl acetate (800 mL). The ethyl acetate solution was washed with 1 M sodium hydroxide (4×200 mL), water (200 mL), and saturated aqueous sodium chloride (200 mL). The organic layer was dried over anhydrous magnesium sulfate and the solvent removed to give a dark oil. The oil was dissolved in tetrahydrofuran (250 mL) and 3 M hydrochloric acid (350 mL) and stirred for 2 hours at room temperature. The reaction solution was extracted with a mixture of diethyl ether/ethyl acetate (2:1, 3×250 mL). Ethyl acetate (300 mL) was added to the aqueous layer and pH was adjusted to 8 with aqueous sodium hydroxide. Layers were separated and the aqueous portion was extracted with another ethyl acetate (3×300 mL). The combined organic extracts were washed with saturated aqueous sodium chloride, dried over anhydrous sodium sulfate, and the solvent removed under vacuum to give a brown residue (12.4 g). The residue was purified by chromatography on silica gel (300 g), eluting with a gradient of ethanol in dichloromethane (1-15%), to give 4-((alpha-R)-alpha-((2S,5R)-4-allyl-2,5-dimethyl-1-piperazinyl)-3-hydroxybenzyl)-N,N-diethylbenzamide as a colorless gum (5.54 g, 27% from 4-formyl-N,N-diethylbenzamide).

4-((alpha-R)-alpha-((2S,5R)-4-Allyl-2,5-dimethyl-1-piperazinyl)-3-hydroxybenzyl)-N,N-diethylbenzamide (4.87 g, 11.2 mmol) was dissolved in methylene chloride (60 mL) and triethylamine (5.15 mL, 3.73 g, 37 mmol) added. N-Phenyl bis(trifluoromethanesulfonimide) (4.40 g, 12.3 mmol) was added and the reaction mixture sealed under nitrogen and stirred at room temperature overnight. The reaction mixture was evaporated to dryness, the residue dissolved in ethyl acetate (100 mL), and the solution extracted with aqueous sodium carbonate solution (5%, 2×75 mL). The organic layer was separated, dried over anhydrous sodium sulfate and evaporated to yield a viscous amber oil. The residue was dissolved in methylene chloride (30 mL), applied to a column of silica gel (1000 g), and eluted with ethanol/methylene chloride (2:98 v/v). Pure fractions containing desired product, as evidenced by t.l.c. (silica gel, EM60F$_{254}$, 2% NH$_4$OH in ethyl acetate, R$_f$=0.78) were evaporated to dryness to yield 4-((alpha-R)-alpha-((2 S, 5R)-4-Allyl-2,5-dimethyl-1-piperazinyl)-3-trifluoromethylsulfonyloxybenzyl)-N,N-diethylbenzamide (4.03 g) as a yellow/amber oil. $^1$H NMR (CDCl$_3$, 500 MHz); δ 1.00 (d, J=6.2 Hz, 3H); 1.12 (br m, 3H); 1.21 (d, J=6.1 Hz, 3H); 1.25 (br m, 3H); 1.83 (t, J=10.6 Hz, 1H); 2.60 (m, 3H); 2.91 (dd J=11.4, 2.7, 1H); 3.02 (m, 1H); 3.18 (br s, 2H); 3.28 (br m, 2H); 3.46 (dd, J=13.7, 5.5 Hz, 1H); 3.55 (br m, 2H); 5.25 (m, 2H); 5.31 (s, 1H); 5.88 (m, 1H); 7.02 (d, J=7.7 Hz, 1H); 7.05 (s, 1H); 7.23 (m, 2H); 7.32 (d, J=8.1 Hz, 2H); 7.40 (d, J=8.1 Hz, 2H); 7.46 (t, J=7.9 Hz, 1H).

A solution of 4-((alpha-R)-alpha-((2S,5R)-4-allyl-2,5-dimethyl-1-piperazinyl)-3-trifluoromethylsulfonyloxybenzyl)-N,N-diethylbenzamide (4.03 g, 7.20 mmol) and thiosalicylic acid (1.32 g, 8.52 mmol) in anhydrous tetrahydrofuran (25 mL) was stirred under nitrogen for 3 h at room temperature with a catalyst solution prepared by dissolution of bis(dibenzylidineacetone)palladium (204 mg, 0.355 mmol) and 1,4-bis(diphenylphosphino)butane (151 mg, 0.355 mmol) in tetrahydrofuran (3 mL). The reaction mixture was evaporated to dryness, the residue dissolved in a mixture of ethyl acetate/ether (1:3, 125 mL) and extracted with aqueous sodium carbonate solution (5%, 2×75 mL). The organic layer was diluted with two volumes of pentane and extracted with 3M-hydrochloric acid (5×25 mL). The aqueous solution was adjusted to pH 9-10 with concentrated ammonia solution and extracted with methylene chloride (3×50 mL). The combined organic extracts were dried over anhydrous sodium sulfate and evaporated to yield 4-((alpha-R)-alpha-((2S,5R)-2,5-dimethyl-1-piperazinyl)-3-trifluoromethyl-sulfonyloxybenzyl)-N,N-diethylbenzamide as a brittle pale yellow foam (3.53 g). The product showed a single spot on thin layer chromatography (silica gel, EM60F$_{264}$, 2% NH$_4$OH in ethyl acetate, R$_f$=0.33). $^1$H NMR (CDCl$_3$, 500 MHz); δ 0.95 (d, J=6 Hz, 3H); 1.13 (br m, 3H); 1.20 (d, J=6.1 Hz, 3H); 1.26 (br m, 3H); 1.50 (t, J=9.7 Hz, 1H); 2.31 (m, 1H); 2.64 (dd J=11.3, 2.5, 1H); 2.71 (m, 1H); 2.95 (m, 1H); 3.29 (br m, 2H); 3.56 (br m, 2H); 5.43 (s, 1H); 7.04 (m, 1H); 7.21 (d, J=7.7, 1H); 7.24 (dd, J=8.2, 2.2 Hz, 1H); 7.34 (d, J=8.2 Hz, 2H); 7.42 (d, J=8.1 Hz, 2H); 7.48 (t, J=8 Hz, 1H).

A solution of 4-((alpha-R)-alpha-((2S,5R)-2,5-dimethyl-1-piperazinyl)-3-trifluoromethyl-sulfonyloxybenzyl)-N,N-diethylbenzamide (3.522 g, 6.0 mmol) and sodium iodide (90 mg, 0.6 mmol) in acetonitrile (30 mL) was stirred during the addition of triethylamine (3.0 mL, 2.186 g, 21.6 mmol) followed by 3-fluorobenzyl bromide (1.472 mL, 2.268 g, 12.0 mmol). An immediate turbidity was observed, thickening to a white crystalline precipitate as the reaction progressed. The reaction mixture was sealed under nitrogen and stirred at room temperature. After 18 h the solvent was removed by evaporation under reduced pressure and the residue partitioned between ethyl acetate (30 mL) and saturated sodium bicarbonate solution (10 mL). The organic layer was separated and the aqueous portion further extracted with ethyl acetate (3×15 mL). The combined organic extract and washings were dried over sodium sulfate, the solution evaporated to dryness and re-dissolved in ethyl acetate (~5 mL). The solution was applied to an intermediate (4×15 cm) Biotage column and eluted with ethyl acetate, collecting fractions of 20 mL. Fractions containing pure material as evidenced by thin layer chromatography (silica, EM60F$_{254}$, developed with ethyl acetate, R$_f$ 0.9) were pooled and evaporated to yield a yellow/orange oil (3.01 g). The oil was dissolved in ethanol (30 mL) and aqueous sodium hydroxide solution (10.0 mL, 2.5-M, 25 mmol) was added. The initially cloudy suspension clarified to a yellow solution that was set aside at room temperature for 3 h. The mixture was evaporated under reduced pressure to remove ethanol, and evaporation continued until condensation of water indicated complete removal of ethanol. The cloudy suspension of the oily sodium salt of the phenol was diluted to 20 mL with water to yield a clear yellow solution. The pH of the strongly basic solution was adjusted to 8.5-9 by passage of carbon dioxide gas (from dry ice) to yield a dense white flocculent precipitate. The solid was removed by filtration and washed thoroughly with cold water, including twice re-slurrying of the precipitate on the sinter with fresh water. The solid was air-dried on the sinter overnight, then dried under vacuum at 1 mm Hg at room temperature to yield 4-((alpha-R)-alpha-((2S,5R)-2,5-dimethyl-4-(3-fluorobenzyl)-1-piperazinyl)-3-hydroxybenzyl)-N,N-diethylbenzamide as a white solid (2.062 g, 67%) Calc. for C$_{31}$H$_{38}$FN$_3$O$_2$ 0.5H$_2$O: C, 72.63; H, 7.67; N, 8.20; F, 3.71. Found C, 72.77; H, 7.52; N, 8.18; F, 3.61%. $^1$H NMR (CDCl3, 300 MHz); δ 1.05 (d, J=5.9 Hz, 6H); 1.11 (br m, 3H); 1.23 (br m, 3H); 2.00 (m, 2H); 2.59 (br m, 2H); 2.62 (d, J=11.4 Hz, 1H); 2.68 (d, J=11.0 Hz, 1H); 3.19 (d, J=13.6 Hz, 1H); 3.28 (br m, 2H); 3.54 (br m, 2H); 3.89 (d, J=13.9 Hz, 1H); 5.01 (s, 1H); 6.15 (v br s, 1H); 6.63 (s, 1H); 6.70 (m, 2H); 6.91 (t, J=8.8 Hz, 1H); 7.07 (m, 2H); 7.14 (t, J=7.8 Hz, 1H); 7.22 (m, 1H); 7.28 (d, J=8.2 Hz, 2H); 7.44 (d, J=8.1 Hz, 2H).

Method B—Reductive Alkylation

A solution of 4-[(R)-((2S,5R)-4-allyl-2,5-dimethyl-1-piperazinyl)-(3-hydroxyphenyl)-methyl]-N,N-diethylbenzamide (10.89 g, 25 mmol, from Method A) and thiosalicylic acid (4.63 g, 30 mmol) in anhydrous tetrahydrofuran (50 mL) was stirred with a catalyst solution prepared by dissolution of bis(dibenzylidineacetone)palladium (0.718 g, 1.25 mmol) and 1,4-bis(diphenylphosphino)butane (0.533 g, 1.25 mmol) in tetrahydrofuran (10 mL) at room temperature under nitrogen for 1.5 hours (J. P. Genet, S. Lemaire-Audoire, M. Savignac, Tetrahedron Letters, 36, 1267-1270 (1995)). The reaction mixture was concentrated under reduced pressure and the residue was partitioned between ethyl acetate (150 mL) and aqueous sodium carbonate solution. The layers were separated and diethyl ether (250 mL) was added to the organic layer. This was extracted with 5% sodium carbonate solution (2×150 mL). The organic layer was diluted with pentane (500 mL) and extracted with 3 M hydrochloric acid (6×30 mL). The aqueous solution was adjusted to pH 9-10 with saturated aqueous sodium carbonate solution and extracted with methylene chloride (3×100 mL). The combined organic extracts were dried over anhydrous sodium sulfate and the solvent was removed under reduced pressure to yield 4-[(R)-((2S,5R)-2,5-dimethyl-1-piperazinyl)-(3-hydroxyphenyl)methyl]-N,N-diethylbenzamide as a brittle pale yellow foam (10.24 g). The product showed a single peak on HPLC (Zorbax C-8, isocratic 40% 0.01 M $NH_4OAc$ in MeOH, 3 min; linear gradient to 100% MeOH, 45 min; isocratic MeOH, 5 min; 1.0 mL/min; $\delta_{obs}$=210 nm, Rt=19.24 min). Calc. for $C_{24}H_{33}N_3O_2$ 0.1 EtOAc 0.4 $CH_2Cl_2$: % C, 67.96; H, 7.96; N, 9.59. Found: % C, 67.90; H, 8.03; N, 9.54. $^1$H NMR ($CDCl_3$, 300 MHz): δ7.42 (d, J=8.1 Hz, 2H); 7.26 (d, J=8.3 Hz, 2H); 7.11 (t, J=7.8 Hz, 1H); 6.72 (d, J=8.1 Hz, 1H); 6.65 (s, 1H); 6.59 (d, J=7.6 Hz, 1H); 5.16 (s, 1H); 4.93 (v br s, 2H); 3.51 (br m, 2H); 3.27 (br m, 2H); 3.02-2.97 (m, 1H); 2.92 (d, J=10.5 Hz, 1H); 2.66 (br d, J=8.5 Hz, 2H); 2.60-2.45 (m, 1H); 1.84 (dd, J=11.3, 8.3 Hz, 1H); 1.27-1.15 (m, 3H); 1.10 (d, J=6.1 Hz, 3H overlapping with m, 3H); 1.02 (d, J=6.1 Hz, 3H).

Glacial acetic acid (0.635 mL, 11.1 mmol) was added to a solution of 4-[(R)-((2S,5R)-2,5-dimethyl-1-piperazinyl)-(3-hydroxyphenyl)methyl]-N,N-diethylbenzamide (1.98 g, 5 mmol) and 3-flourobenzaldehyde (1.24 g, 10 mmol) in anhydrous tetrahydrofuran (35 mL). While stirring briskly, sodium triacetoxyborohydride (2.12 g, 10 mmol) was added in 50-100 mg portions, allowing effervescence to subside after each addition. The reaction was monitored for absence of starting material by HPLC. After stirring at room temperature for 16 hours, additional 3-fluorobenzaldehyde (0.62 g, 5 mmol), acetic acid (0.318 mL, 5 mmol), and sodium triacetoxyborohydride (1.06 g, 5 mmol) were added. After stirring an additional 4 hours, the reaction mixture was concentrated under reduced pressure and the residue was partitioned between ethyl acetate (50 mL) and 3 M hydrochloric acid (25 mL). The layers were separated and the organic layer was extracted again with 3 M hydrochloric acid (25 mL). The aqueous solution was adjusted to pH 9-10 with 5 M sodium hydroxide solution, resulting in the formation of chunky white precipitate. Brief sonication followed by continuous stirring for 60 hours allowed hydrolysis of any residual ethyl acetate, as well as complete precipitation of product. The white solid was filtered, washed with cold water, and further dried under reduced pressure to yield 4-[(R)-((2S,5R)-2,5-dimethyl-4-(3-fluorobenzyl)-1-piperazinyl)(3-hydroxyphenyl)-methyl]-N,N-diethylbenzamide (1.78 g, 82.3% yield from 4-[(R)-((2S,5R)-4-allyl-2,5-dimethyl-1-piperazinyl)-(3-hydroxyphenyl)-methyl]-N,N-diethyl-benzamide). The product showed a single peak on HPLC (Zorbax C-8, isocratic 40% 0.01 M $NH_4OAc$ in MeOH, 3 min; linear gradient to 100% MeOH, 45 min; isocratic MeOH, 25 min; 1.0 mL/min; $\delta_{obs}$=210 nm, Rt=43.51 min). Calc. for $C_{31}H_{38}FN_3O_2 \cdot 0.5H_2O$: % C, 72.63; H, 7.67; N, 8.20; F, 3.71. Found: % C, 72.77; H, 7.52; N, 8.18; F, 3.61.

Method C—Direct Alkylation

To 4-[(R)-((2S,5R)-2,5-dimethyl-1-piperazinyl)-(3-hydroxyphenyl) methyl]-N,N-diethyl-benzamide (0.79 g, 2 mmol) and sodium iodide (30 mg, 0.2 mmol) in acetonitrile (10 mL) was added triethylamine (1.0 mL, 7.2 mmol), followed by 3-fluorobenzylbromide (0.76 g, 4 mmol). The reaction mixture was sealed under nitrogen and stirred at ambient temperature for 20 hours. The reaction mixture was concentrated under reduced pressure and the residue was partitioned between ethyl acetate (150 mL) and saturated sodium carbonate solution (15 mL) diluted with water (50 mL). The organic layer was separated and the aqueous layer was extracted with ethyl acetate (3×75 mL). The combined organic extracts were dried over anhydrous sodium sulfate and magnesium sulfate. The solvent was removed under reduced pressure to yield a light yellow solid (0.90 g). This solid was dissolved in isopropanol (30 mL) upon heating to boiling, and water (20 mL) was added slowly while swirling and keeping the solution hot. Crystallization occurs as solution begins to cool. Crystallization was allowed to proceed overnight. Crystals were collected and washed sparingly with isopropanol:water/1:1. Drying under 5 mm Hg at 40° C. for 48 hours yielded 4-[(R)-((2S,5R)-2,5-dimethyl-4-(3-fluorobenzyl)-1-piperazinyl)(3-hydroxyphenyl)methyl]-N,N-diethyl-benzamide as old ivory colored crystals (0.77 g, 76.4% from 4-[(R)-((2S,5R)-4-allyl-2,5-dimethyl-1-piperazinyl)-(3-hydroxyphenyl)-methyl]-N,N-diethylbenzamide). Calc. for $C_{31}H_{38}FN_3O_2 \cdot 0.25H_2$ O·0.1$^i$ PrOH: % C, 73.12; H, 7.70; N, 8.17; F, 3.69. Found: % C, 73.13; H, 7.73; N, 8.24; F, 3.53.

Method D—Assembly from (2R,5S)-1-(3-fluorobenzyl)-2,5-dimethylpiperazine

In a 3 L round bottom flask fitted with a condenser and Dean-Stark trap are combined 4-formyl-N, N-diethylbenzamide (20.53 g, 100 mmol), benzotriazole (11.91 g, 100 mmol), and (2R,5S)-1-(3-flourobenzyl)-2,5-dimethylpiperazine (22.23 g, 100 mmol, Chirotech Division of Dowpharma, The Dow Chemical Company, Cambridge, England) with 1000 mL of toluene. The reaction is heated to reflux under nitrogen until no additional water is observed in the trap (ca. 3 hours). The reaction is cooled to room temperature and concentrated under vacuum to leave a volume of approximately 300 mL. Anhydrous tetrahydrofuran (500 mL) is added to the benzotriazole adduct under nitrogen with stirring until dissolved. To this solution is added to the solution of 3-tert-butyldimethylsilyloxyphenylmagnesium bromide (from Method A) at room temperature via double-ended needle. After stirring for approximately 2 hours, the reaction is quenched by the addition of saturated aqueous ammonium chloride solution (50 mL) and stirred for 15 minutes. Anhydrous magnesium sulfate (50 g) is added, stirred for approximately 1 hour, and the reaction is filtered. The solvent is removed under reduced pressure and the residue is dissolved in ethyl acetate (1000 mL). The ethyl acetate solution is washed with 1 M sodium hydroxide (5×400 mL), water (4×400 mL), and saturated aqueous sodium chloride solution (400 mL). The organic layer is dried over anhydrous magnesium sulfate and the solvent is removed to give a viscous oil. The oil is dissolved in 500 mL of tetrahydrofuran and 300 mL of 3 M hydrochloric acid and stirred for approximately 1.5 hours at room temperature. Upon completion of the desilylation, the reaction is diluted with water (300 mL) and concentrated under vacuum to about half the original volume. This solution is extracted with pentane (2×500 mL). The aqueous layer is adjusted to pH 8-9 with 5 M sodium hydroxide and extracted with ethyl acetate (250 mL). The layers are separated and the aqueous portion is extracted with more ethyl acetate (250 mL). The combined organic extracts are washed with saturated aqueous sodium chloride solution, dried over anhydrous sodium sulfate, and the solvent is removed under reduced pressure to give a viscous oil. This residue is dissolved in ethyl acetate (25 mL), seeded with crystals of the authentic compound, and allowed to crystallize overnight (seed crystals can be obtained from hot 2-propanol with addition of water). The crystals are filtered and washed sparingly with cold ethyl acetate. Drying under 5 mm Hg at room temperature yields the desired product 4-[(R)-((2 S, 5R)-4-(3-fluorobenzyl)-2,5-dimethyl-1-piperazinyl)-(3-hydroxy-phenyl)-methyl]-N,N-diethylbenzamide as tan to off-white crystals, free from the undesired epimer. This solid is dissolved in isopropanol (300 mL) upon heating to boiling, and water (200 mL) is added slowly while swirling and keeping the solution hot. Crystallization occurs as solution begins to cool and is allowed to proceed overnight. Crystals are collected and washed sparingly with cold isopropanol:water/ 1:1. Drying under 5 mm Hg at 40° C. for 48 hours yields 4-[(R)-((2S,5R)-2,5-dimethyl-4-(3-fluorobenzyl)-1-piperazinyl)(3-hydroxyphenyl)methyl]-N,N-diethyl-benzamide as ivory colored crystals (expected yield ~30% from 4-formyl-N,N-diethylbenzamide).

Example 2

Monotherapy with Formula (i) in L-DOPA Naïve MPTP-Lesioned Macaques and MPTP-Lesioned Macaques with Established Motor Complications.

Eight cynomolgus monkeys (*Macaca fascicularis*, 6.4-6.8 years of age, 2.8-4.2 kg were used in this study. Animals were housed two or three per cage in the same housing room. The housing rooms were subject to a 12 hour light-dark cycle (lights on 7 a.m.), temperature 20-25° C. in a room containing only animals of the same sex. Fresh fruit, primate pellets and water were available ad libitum other than at times of overnight fasting prior to PK or behavioral assessment days.

The animals were rendered parkinsonian via once-daily subcutaneous injection of MPTP (0.2 mg/kg), administered for between 9 and 12 days, until the appearance of parkinsonism symptoms. After this time, a parkinsonian syndrome reached a moderate to marked level, over approximately 30 days, and stabilized. The monkeys were allowed to recover for a minimum of further 40 days until their parkinsonism was demonstrated as being stable. L-DOPA naïve animals have received no L-DOPA and those showing established motor complication have received L-DOPA in an amount 25 mg/kg orally twice daily for at least 2 months. L-DOPA is given with the decarboxylase inhibitor benserazide (as Madopar™).

Activity

In L-DOPA naïve MPTP-lesioned macaques Formula (i) resulted in a significant increase in activity counts during the second hour (10 and 20 mg/kg, by 62% and 63% respectively) and third hour (20 mg/kg only, by 82%) of observation (third and fourth hours after administration) compared to that seen following vehicle treatment. In L-DOPA naïve MPTP-lesioned macaques, levels of activity observed following treatment with vehicle averaged 2249±658 counts over the 0-6 h period of observation. Examining the whole 6 h time-course period of observation revealed no significant effect of Formula (i) treatment (F (3, 21)=0.6734, P=0.5779) or the interaction of treatment and time (F (15, 105)=1.295, P=0.2184) but did show an effect of time alone (F (5, 35)=7.928, P<0.0001) on levels of activity (2-way, RM-ANOVA, FIG. 1A). Post-hoc Holm-Sidak's analysis revealed a significant increase in activity in the 1-2 h period following start of observations (2-3 h period following treatment) with 10 and 20 mg/kg doses of Formula (i) (by 62% and 63%, P<0.05 and P<0.01 respectively cf. vehicle) while in the 2-3 h period there was a significant increase in activity levels (by 82%) in response to high-dose Formula (i) (20 mg/kg; P<0.05 cf. vehicle). Examining levels of average activity cumulated over each of the three-hour periods 0-3 and 3-6 h after start of observations revealed no significant effect of Formula (i) treatment during either period (0-3 h; F (1.170, 8.189)=0.9758, P=0.3672, 3-6 h; F (1.262, 8.836)= 0.4690, P=0.5550, FIGS. 1B and 1C).

Figure 2:
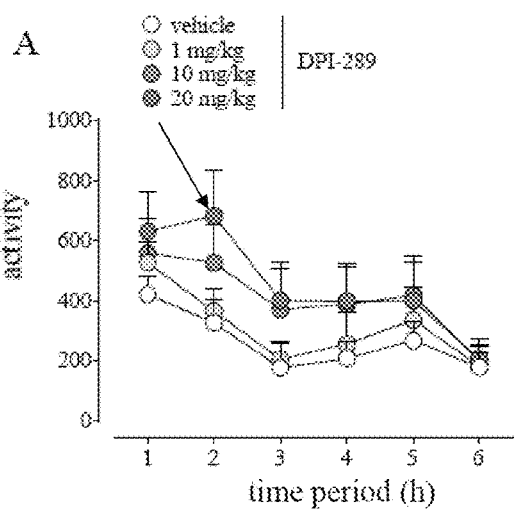
FIG. 2 shows the results on movement activity of administration of DPI-289 in macaques with established motor complications due to administered L-DOPA. This activity is measured by an infra-red movement detector and captures all movement, normal and abnormal. Data are mean±s.e.m.
Figure 2:
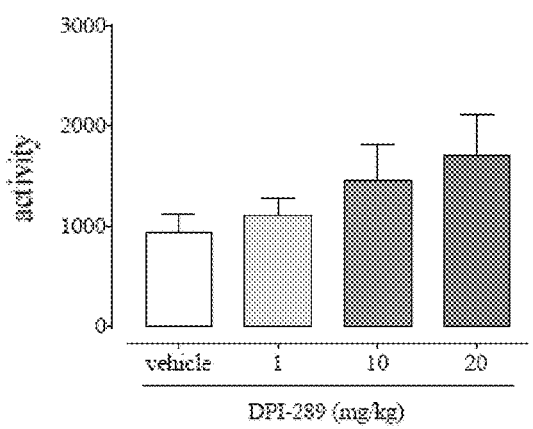
Figure 2:
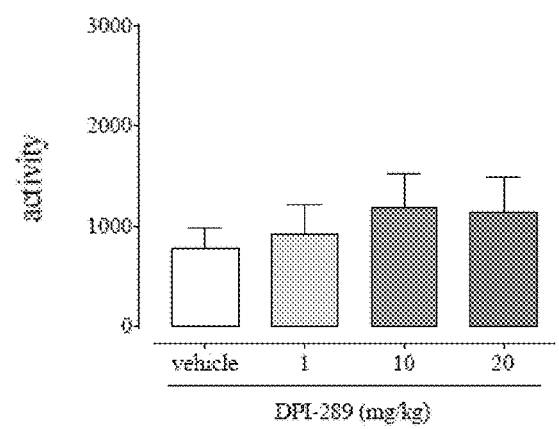

FIG. 2 shows the results of administration of DPI-289 in macaques with established motor complications due to administered L-DOPA and there is an increase in activity relative to the vehicle in the first few hours which decreased in the 3 to 6 hours after administration of the DPI-289. Clearly the oral administration of single dose of 10 or 20 mg/kg of DPI 289 significantly alleviated motor impairment for 1 to 4 hours. The differences in results of FIGS. 1A and 2A are primarily due to differences in response to the vehicle.

Total ON-Time

Figure 3:
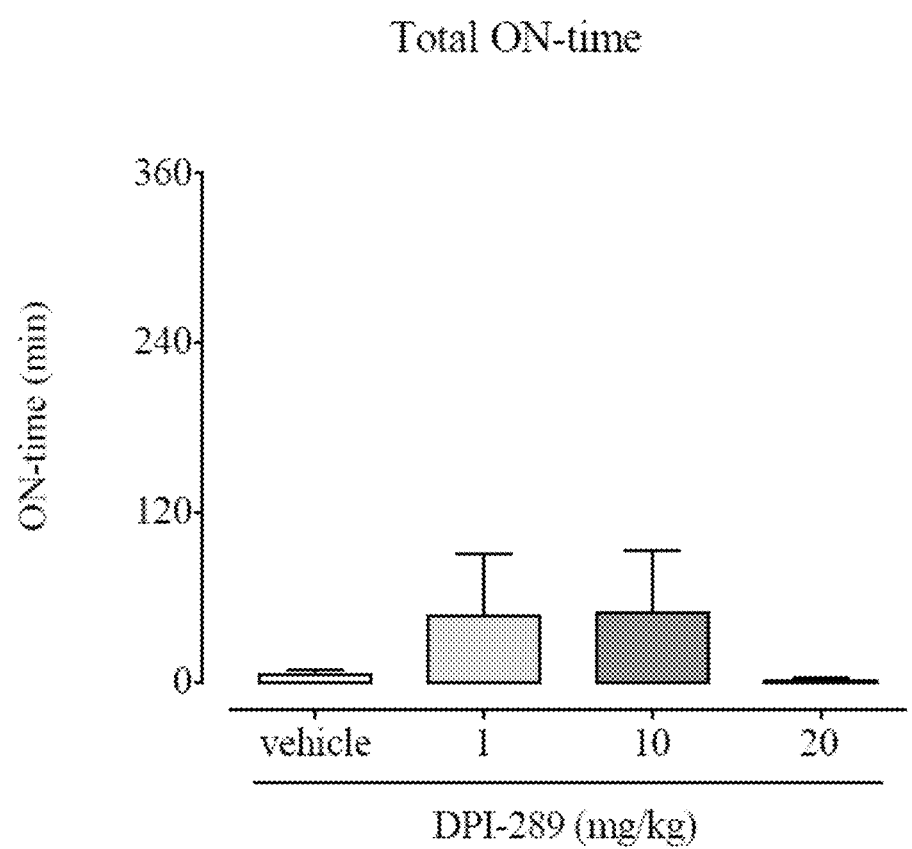
FIG. 3 shows effect of Formula (i) (DPI-289) on duration of ON-time in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Levels of bradykinesia were assessed every 10 min over the entire 6 h observation and total duration of ON-time (minutes for which bradykinesia was absent) was calculated. Data are mean±s.e.m. N=8 for all treatment groups. All P>0.05, cf vehicle-treatment; 1-way, RM-ANOVA with Holm-Sidak's Multiple Comparison test.
Figure 4:
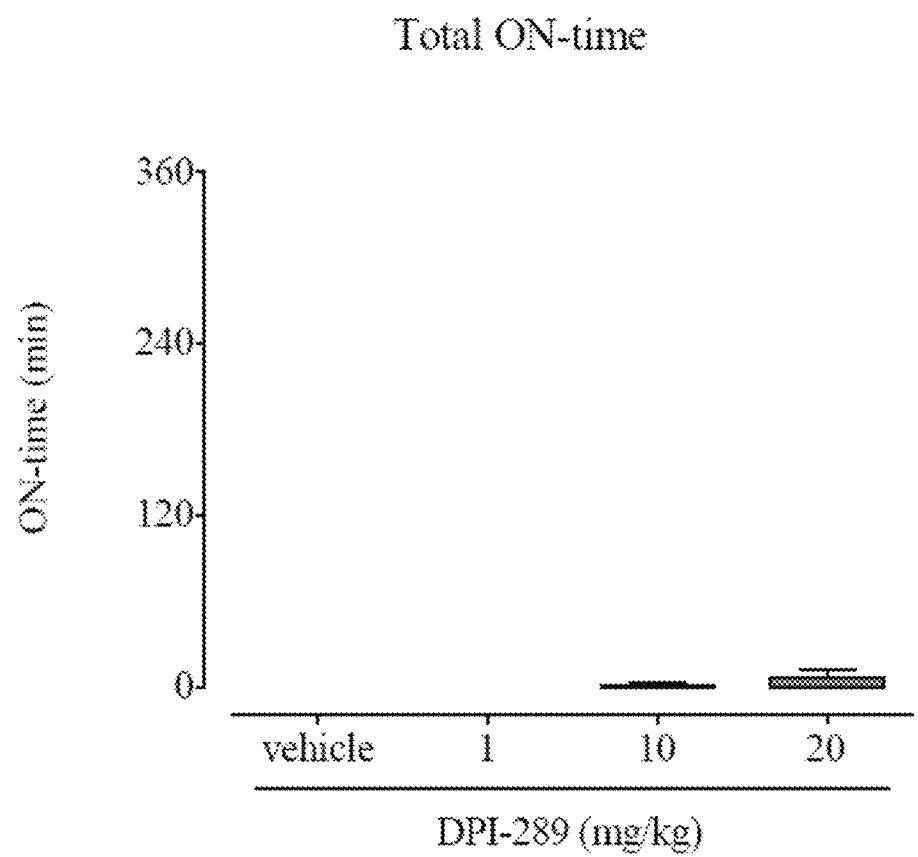
FIG. 4 shows the results of administration of DPI-289 in macaques with established motor complications due to administered L-DOPA.

In L-DOPA naïve MPTP-lesioned macaques Formula (i) administration provided no significant increase in total duration of ON-time at any dose assessed. (On-time is defined as the number of minutes wherein no bradykinesia (slowness of movement) is observed) L-DOPA naïve MPTP-lesioned macaques treated with vehicle, displayed a mean total duration of ON-time of 5±4 min. There was no significant effect of DPI-289 treatment on total ON-time between the 1 and 10 mg/kg; 1 mg/kg; 46±48 min, 10 mg/kg; 49±48 min, 20 mg/kg; 1±1 min (F (1.002, 7.016)=1.106, P=0.3281, one-way, RM-ANOVA, FIG. 3). FIG. 4 shows the results of administration of DPI-289 in macaques with established motor complications due to administered L-DOPA and with only limited on-time at a dose of 20 mg/kg of DPI-289. ON-time represents lack of bradykinesia so mere improvement in bradykinesia would not be reflected in changes in ON-time. The oral bioavailability of the drug in these animals was only 1-2% so the lack of effect on ON-time is likely due to inadequate systemic exposure levels. Higher systemic levels of the drug may have a more profound effect on bradykinesia and which could translate into changes in ON-time.

Parkinsonian Disability

Figure 5:
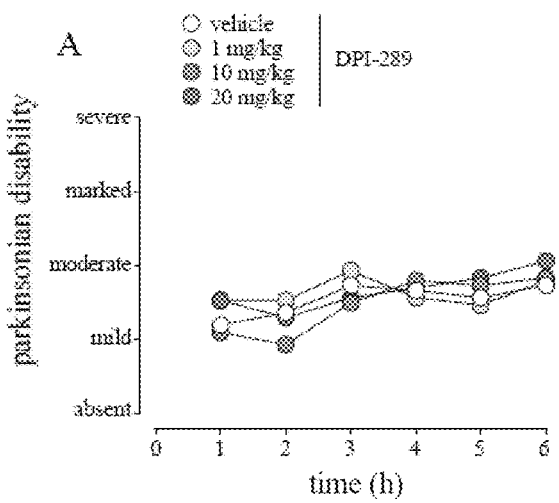
FIG. 5 shows effect of Formula (i) (DPI-289) on parkinsonian disability in L-DOPA naïve MPTP-lesioned primates. Parkinsonian disability is scored by a trained neurologist who is blinded to treatment allocation but is trained to differentiate normal from abnormal movements and is able to distinguish diminution of Parkinsonian disability from dyskinetic (abnormal) movements. MPTP-lesioned cynomolgus monkeys received acute oral administration of either vehicle or Formula (i) (1, 10 or 20 mg/kg) according to a randomized incomplete Latin Square-type. Levels of parkinsonian disability were assessed every 10 min over the entire 6 h observation. Data are median values (FIG. 5A shows time-course) or median bars with individual animal scores (cumulated 0-3 h shown in FIG. 5B or 3-6 h shown in FIG. 3C). N=8 for all treatment groups. */P<0.05 cf. vehicle-treatment; 2-way RM ANOVA of ranked data (FIG. 5A) or 1-way RM-ANOVA with Holm-Sidak's Multiple Comparison test (FIGS. 5B and C).
Figure 5:
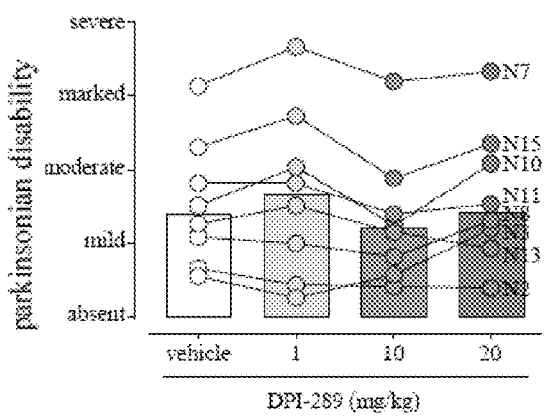
Figure 5:
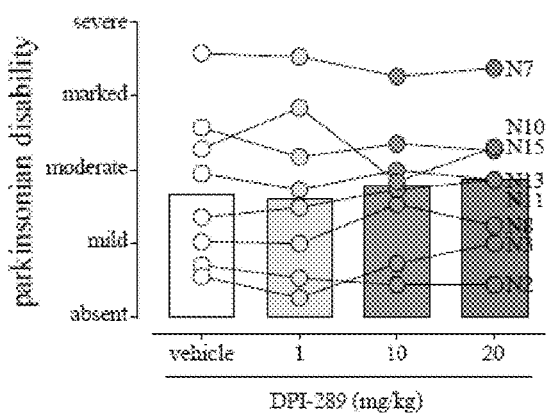

In L-DOPA naïve MPTP-lesioned macaques Formula (i) (10 mg/kg) provided a modest but significant reduction in parkinsonian disability (to absent-mild levels) during the second hour of observation (third hour after administration) compared to vehicle treatment (mild-moderate levels). In L-DOPA naïve MPTP-lesioned macaques, levels of parkinsonian disability observed following treatment with vehicle were of mild to moderate levels during the 0-6 h period of observation. Examining the whole 6 h time-course period of observation revealed no significant effect of DPI-289 treatment (F (3, 28)=1.004, P=0.4057) or time (F (5, 140)=0.0, P>0.9999) but did show a significant effect of the interaction of the two (F (15, 140)=2.062, P=0.0151) on levels of disability (2-way, RM-ANOVA, FIG. 5A). Post-hoc Holm-Sidak's analysis revealed a significant decrease in disability to absent-mild levels in the 1-2 h period of observation (2-3 h following treatment with DPI-289, 10 mg/kg only, P<0.05 cf. vehicle; mild-moderate levels). Examining levels of average parkinsonism cumulated over each of the three-hour periods 0-3 and 3-6 h after start of observations revealed no significant effect of DPI-289 treatment during either period (0-3 h; Friedman Statistic (FS)=5.582, P=0.1338, 3-6 h; FS=1.71, P=0.635, Friedman test, FIGS. 5B and 5C).

Figure 6:
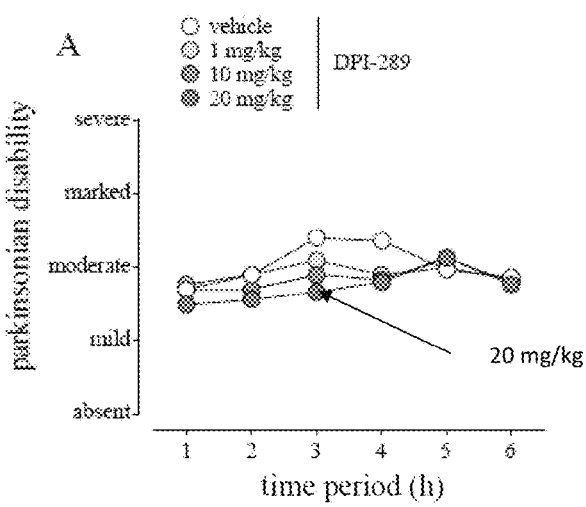
FIG. 6 shows the results of administration of DPI-289 in macaques with established motor complications due to administered L-DOPA. Parkinsonian disability is scored by a trained neurologist who is blinded to treatment allocation but is trained to differentiate normal from abnormal movements and is able to distinguish diminution of Parkinsonian disability from dyskinetic (abnormal) movements. Data are mean±s.e.m.
Figure 6:
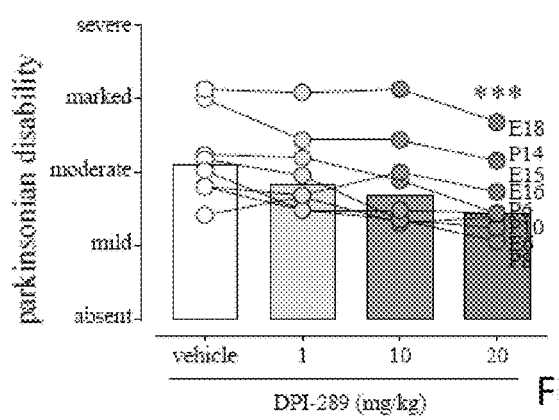
Figure 6:
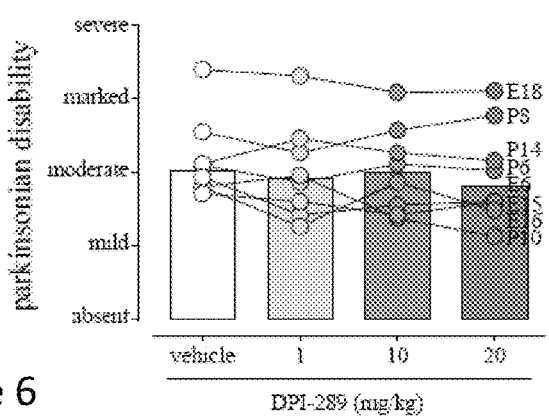

FIG. 6A shows the results of administration of DPI-289 in macaques with established motor complications due to administered of L-DOPA with a significant reduction in parkinsonian disability at a dose of 20 mg of/kg of DPI-289 in two to three hours after dosing with DPI-289 (FIG. 6B). Overall, there was a dose effect of DPI 289 on parkinsonian disability and a single dose of 20 mg/kg had an effect for about 4 hours.

Bradykinesia

Figure 7:
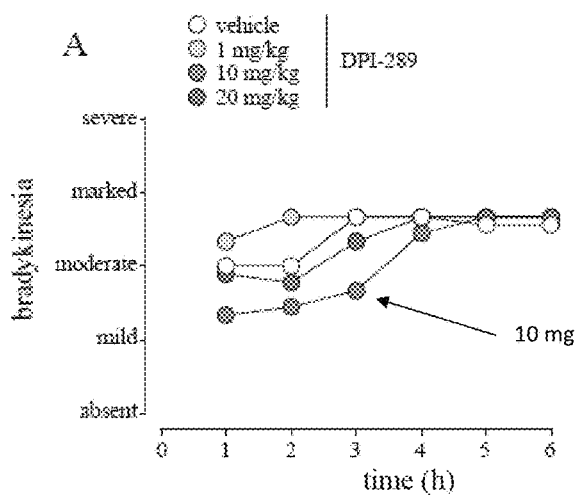
FIG. 7 shows effect of Formula (i) (DPI-289) on bradykinesia in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Levels of bradykinesia were assessed every 10 min over the entire 6 h observation. Data are median values (FIG. 7A shows time-course) or median bars with individual animal scores (cumulated for 0-3 h shown in FIG. 7B or 3-6 h shown in FIG. 7C). N=8 for all treatment groups. */** represents P<0.05 or P<0.01 cf. vehicle-treatment; 2-way RM ANOVA of ranked data (FIG. 7A) or 1-way RM-ANOVA with Holm-Sidak's Multiple Comparison test (FIGS. 7B and 7C).
Figure 7:
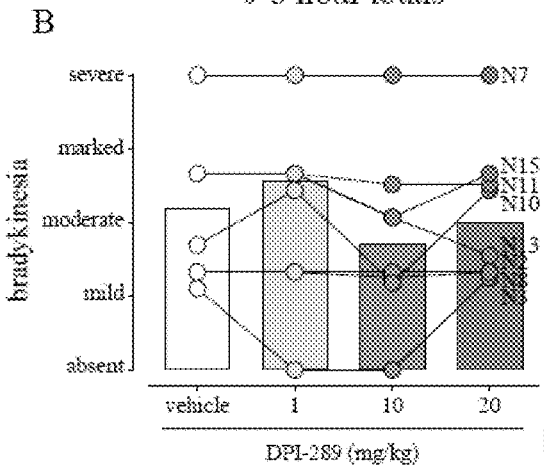
Figure 7:
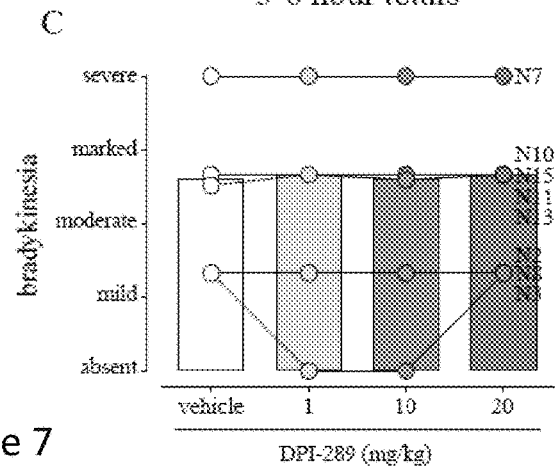

In L-DOPA naïve MPTP-lesioned macaques Formula (i) (10 mg/kg) provided a significant reduction in levels of bradykinesia (to mild-moderate levels) during the first four hours of observation (1-5 hours after administration) compared to vehicle treatment (moderate-marked levels). In L-DOPA naïve MPTP-lesioned macaques, levels of bradykinesia observed following treatment with vehicle were of moderate to marked levels during the 0-6 h period of observation. Examining the whole 6 h time-course period of observation revealed a significant effect of Formula (i) treatment (F (3, 28)=3.029, P=0.0459) and the interaction of time and treatment (F (15, 140)=2.236, P=0.0077) but not time alone (F (5, 140)=0.0, P>0.9999) on levels of bradykinesia (2-way, RM-ANOVA, FIG. 7A). Post-hoc Holm-Sidak's analysis revealed a significant decrease in bradykinesia to mild-moderate levels in the 0-1, 1-2, 2-3 and 3-4 h periods of observation (1-2, 2-3, 3-4 and 4-5 h following treatment with DPI-289; 10 mg/kg only, all P<0.05 cf. vehicle). Examining levels of average bradykinesia cumulated over the first three-hour period (0-3 h) after start of observations revealed a significant effect of DPI-289 treatment (0-3 h; Friedman Statistic (FS)=8.681, P=0.034, Friedman test, FIG. 7B). However, post-hoc Dunn's analysis was unable to distinguish any difference between the four treatment groups (all P>0.05). During the 3-6 h period after start of observations there were no significant effects of DPI-289 treatment (3-6 h; Friedman Statistic (FS)=4.385, P=0.2228, Friedman test, FIG. 7C).

Figure 8:
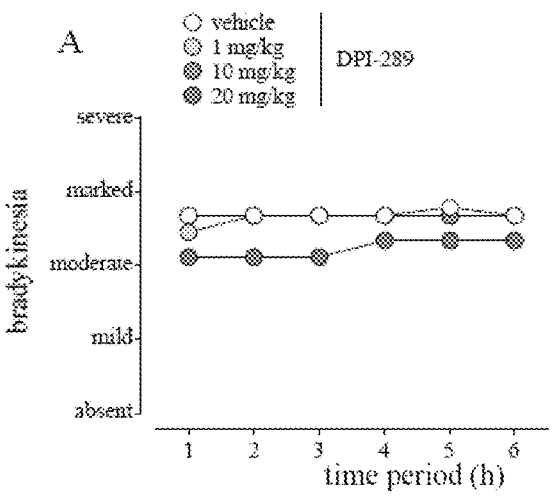
FIG. 8 shows the results of administration of DPI-289 in macaques with established motor complications due to administered L-DOPA. Data are mean±s.e.m.
Figure 8:
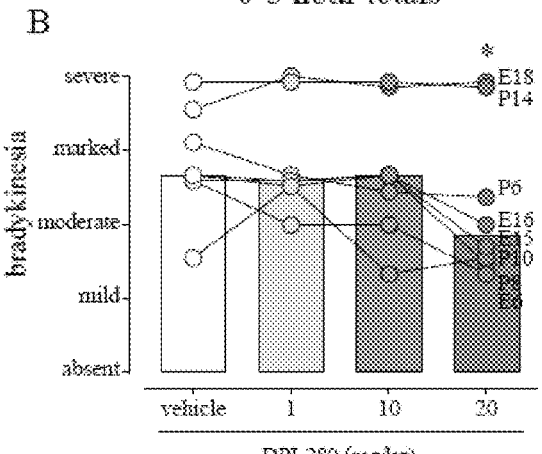
Figure 8:
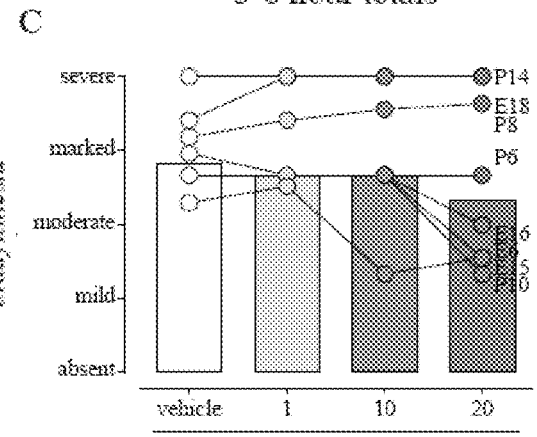

FIG. 8 shows the results of administration of DPI-289 in macaques with established motor complications (bradykinesia) due to administered L-DOPA with a significant change only in the first hour at a dose of 20 mg of/kg of DPI-289 as shown in FIG. 8A.

Range of Movement

Figure 9:
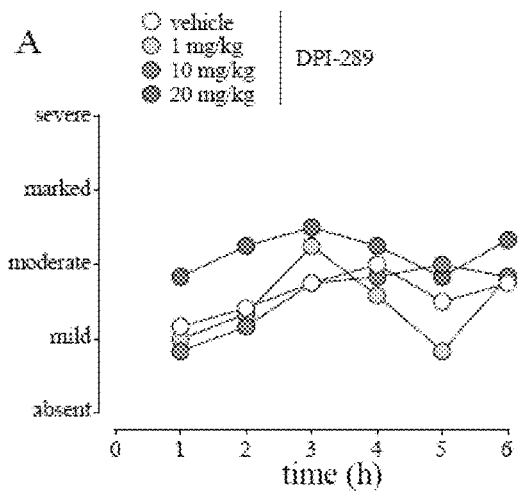
FIG. 9 shows effect of Formula (i) (DPI-289) on range of movement in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Levels of range of movement were assessed every 10 min over the entire 6 h observation. Data are median values (FIG. 9A shown for time-course) or median bars with individual animal scores (cumulated for 0-3 h shown in FIG. 9B or for 3-6 h shown in FIG. 9C). N=8 for all treatment groups. All P>0.05 cf. vehicle-treatment; 2-way RM ANOVA of ranked data (FIG. 9A) or 1-way RM-ANOVA with Holm-Sidak's Multiple Comparison test (FIG. 9B and FIG. 9C).
Figure 9:
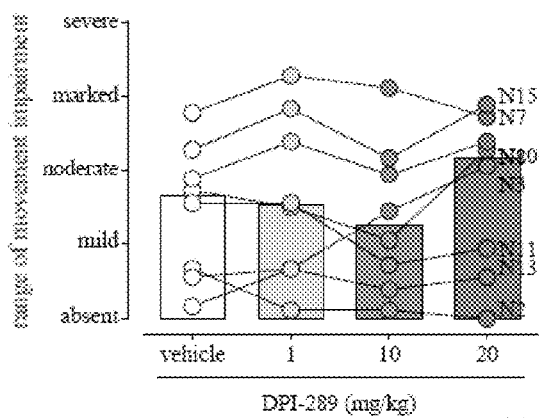
Figure 9:
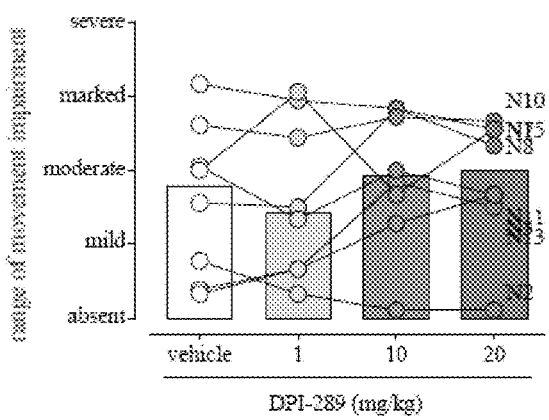

In L-DOPA naïve MPTP-lesioned macaques Formula (i) administration resulted in no reduction in levels of impaired range of movement at any dose assessed. Equally, at no time during the study did treatment with Formula (i) decrease range of movement. In L-DOPA naïve MPTP-lesioned macaques, levels of range of movement observed following treatment with vehicle were typically of mild to moderate levels during the 0-6 h period of observation. Examining the whole 6 h time-course period of observation revealed no significant effect of Formula (i) treatment (F (3, 28)=0.6160, P=0.6104), time (F (5, 140)=0.0, P>0.9999) or the interaction of the two (F (15, 140)=1.215, P=0.2670) on levels of range of movement (2-way, RM-ANOVA, FIG. 9A). Examining average levels of range of movement cumulated over each of the three-hour periods 0-3 and 3-6 h after start of observations revealed no significant effect of DPI-289 treatment during either period (0-3 h; Friedman Statistic (FS)= 4.13, P=0.248, 3-6 h; FS=1.18, P=0.759, Friedman test, FIGS. 9B and 9C).

Figure 10:
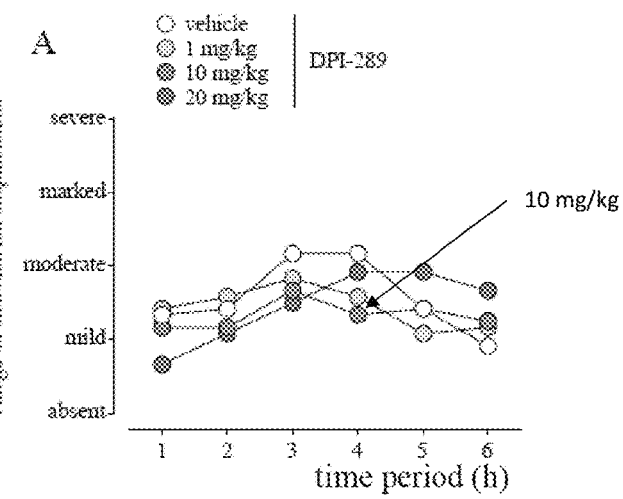
FIG. 10 shows the results of administration of DPI-289 in macaques with established motor complications due to administered L-DOPA. Data are mean±s.e.m.
Figure 10:
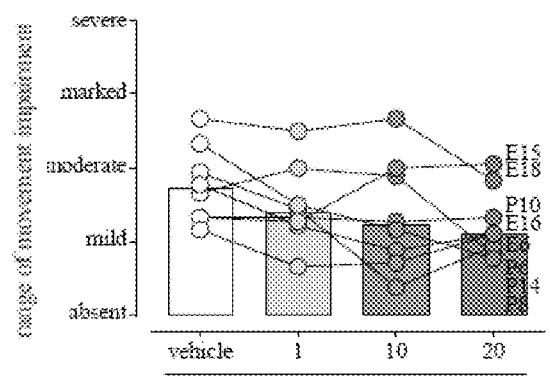
Figure 10:
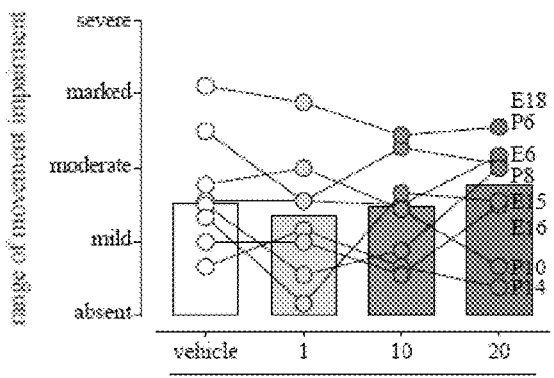

FIG. 10 shows the results of administration of DPI-289 in macaques with established motor complications due to administered L-DOPA with an increase in the range of movement three to four hours after a dose of 1, 10 or 20 mg of/kg of DPI-289 shown in FIG. 10A.

Postural Impairment

Figure 11:
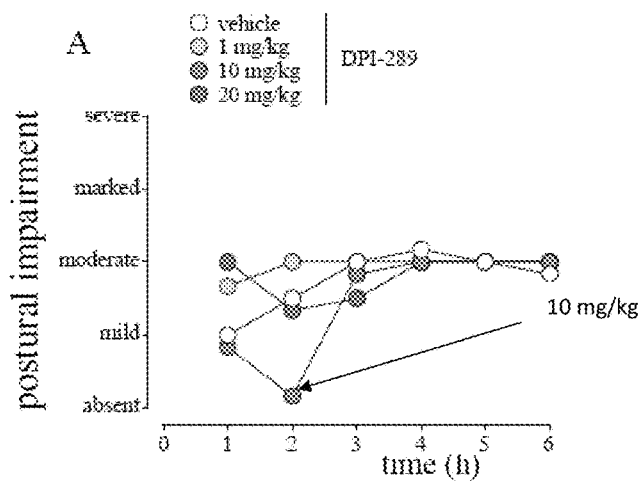
FIG. 11 shows effect of Formula (i) (DPI-289) on postural impairment in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Postural impairment was assessed every 10 min over the entire 6 h observation. Data are median values (FIG. 11A shows time-course) or median bars with individual animal scores (cumulated for 0-3 h shown in FIG. 11B, or for 3-6 h shown in FIG. 11C). N=8 for all treatment groups. **/P<0.01 cf. vehicle-treatment; 2-way RM ANOVA of ranked data (FIG. 11A) or 1-way RM-ANOVA with Holm-Sidak's Multiple Comparison test (FIGS. 11B and C).
Figure 11:
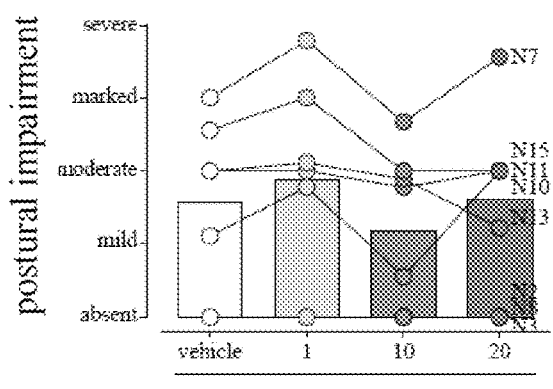
Figure 11:
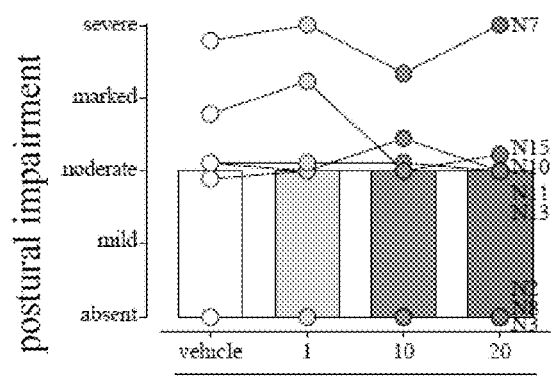

In L-DOPA naïve MPTP-lesioned macaques Formula (i) (10 mg/kg) provided a significant reduction in postural impairment (to absent-mild levels) during the second hour of observation (third hour following administration) compared to vehicle treatment (mild-moderate levels). In L-DOPA naïve MPTP-lesioned macaques, levels of postural impairment observed following treatment with vehicle were of moderate to marked levels during the 0-6 h period of observation. Examining the whole 6 h time-course period of observation revealed a significant effect of Formula (i) treatment (F (3, 28)=3.733, P=0.0225) and the interaction of time and treatment (F (15, 140)=1.776, P=0.0437) but not time alone (F (5, 140)=0.0, P>0.9999) on levels of postural impairment (2-way, RM-ANOVA, FIG. 11A). Post-hoc Holm-Sidak's analysis revealed a significant decrease in postural impairment to absent-mild levels in the 1-2 h period of observation (2-3 h following treatment with DPI-289; 10 mg/kg only, P<0.01 cf. vehicle).

Examining levels of average postural impairment cumulated over the first three-hour period (0-3 h) after start of observations revealed a significant effect of Formula (i) treatment (0-3 h; Friedman Statistic (FS)=8.87, P=0.031, Friedman test, FIG. 11B). However, post-hoc Dunn's analysis was unable to distinguish any difference between the four treatment groups all P>0.05). During the 3-6 h after start of observations there were no significant effects of Formula (i) treatment (3-6 h; Friedman Statistic (FS)=1.350, P=0.717, Friedman test, FIG. 11C.

Figure 12:
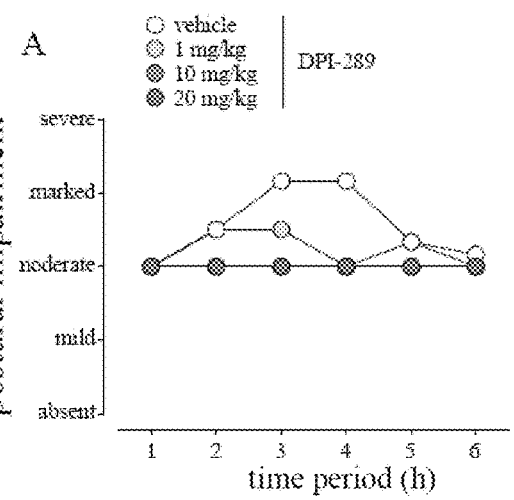
FIG. 12 shows the results of administration of DPI-289 in macaques with established motor complications due to administered L-DOPA. Data are mean±s.e.m.
Figure 12:
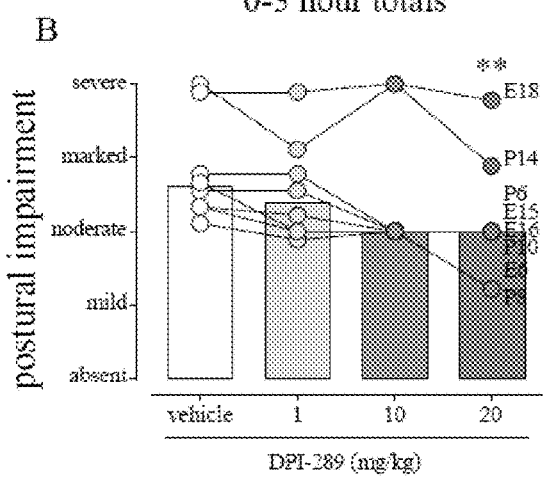
Figure 12:
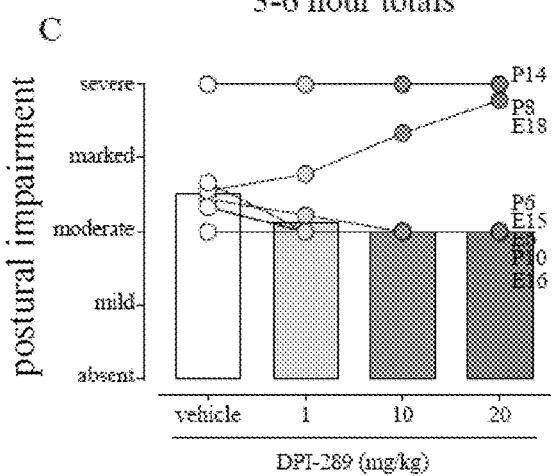

FIG. 12 shows the results of administration of DPI-289 in macaques with established motor complications due to administered L-DOPA with a significant reduction in postural impairment at a dose of 1, 10 and 20 mg of/kg of DPI-289 in two to four hours after dosing with DPI-289 shown in FIG. 12A.

Alertness

Figure 13:
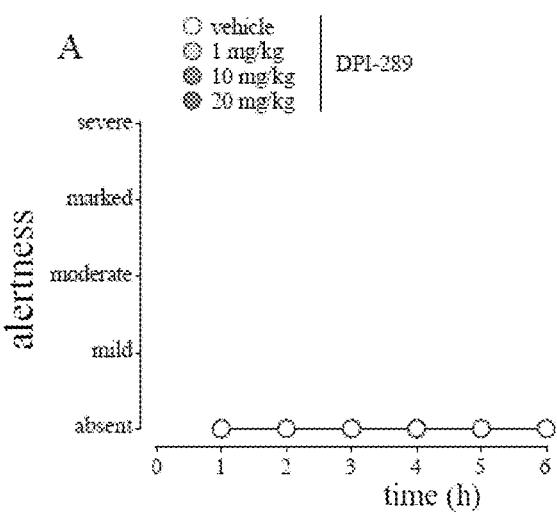
FIG. 13 shows effect of Formula (i) (DPI-289) on alertness in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Alertness was assessed every 10 min over the entire 6 h observation. Data are median values (FIG. 13A shows time-course) or median bars with individual animal scores (cumulated for 0-3 h shown in FIG. 13B or for 3-6 h shown in FIG. 13C). N=8 for all treatment groups. All P>0.05 cf. vehicle-treatment; 2-way RM ANOVA of ranked data (FIG. 13A) or 1-way RM-ANOVA with Holm-Sidak's Multiple Comparison test (FIGS. 13B and C).
Figure 13:
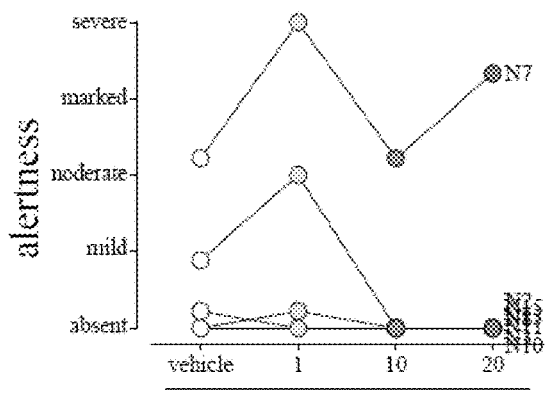
Figure 13:
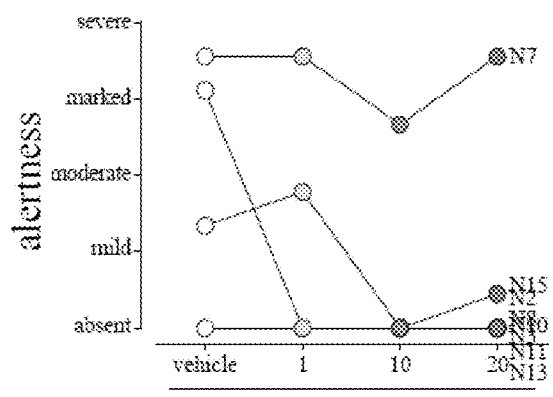

In L-DOPA naïve MPTP-lesioned macaques Formula (i) administration resulted in no increase in levels of alertness at any dose assessed. Equally, at no time during the study did treatment with Formula (i) exacerbate any deficits in alertness. In L-DOPA naïve MPTP-lesioned macaques, average levels of alertness observed following treatment with vehicle were of absent to mild levels during the 0-6 h period of observation. Examining the whole 6 h time-course period of observation revealed no significant effect of Formula (i) treatment (F (3, 28)=2.493, P=0.0806) or time (F (5, 140)= 0.0, P>0.9999) but did show a significant effect of the interaction of the two (F (15, 140)=1.786, P=0.0422) on levels of alertness (2-way, RM-ANOVA, FIG. 13A). Examining average levels of alertness cumulated over each of the three-hour periods 0-3 FIG. 13B and 3-6 h FIG. 13C after start of observations revealed no significant effect of Formula (i) treatment during either period (0-3 h; Friedman Statistic (FS)=5.5, P=0.1386, 3-6 h; FS=5.73, P=0.1257, Friedman test, FIGS. 13B and 13C).

Figure 14:
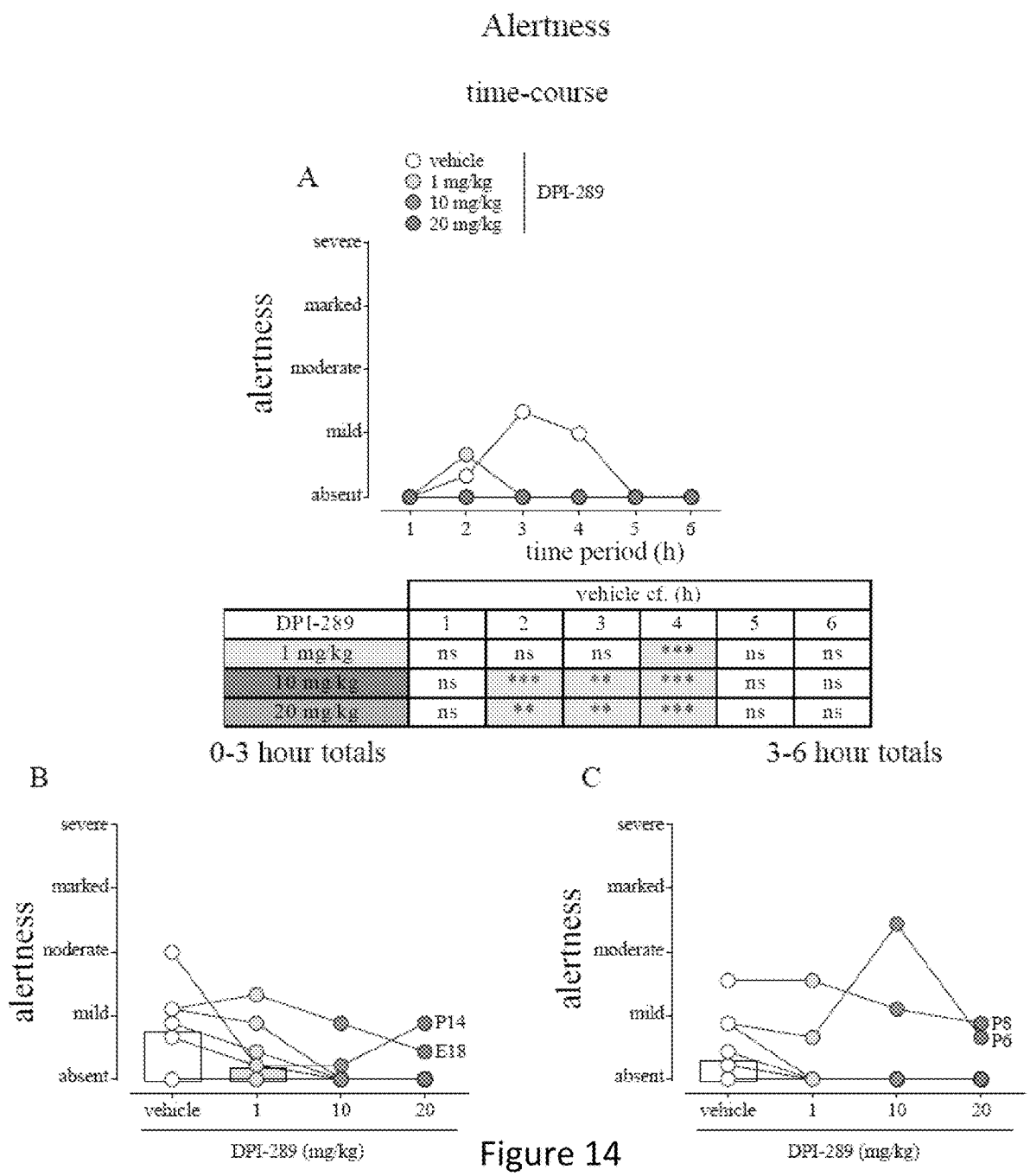
FIG. 14 shows the results of administration of DPI-289 in macaques with established motor complications due to administered L-DOPA. Data are mean±s.e.m.

FIG. 14 shows the results of administration of DPI-289 in macaques with established motor complications due to administered L-DOPA with a significant reduction in deficits in alertness at a dose of 10 or 20 mg of/kg of DPI-289 in two to four hours after dosing with DPI-289 as shown in FIG. 14A.

Dyskinesia

Figure 15:
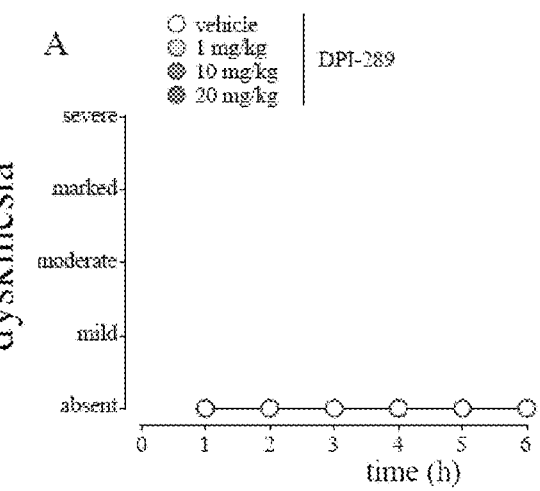
FIG. 15 shows effect of Formula (i) (DPI-289) on dyskinesia in L-DOPA naïve MPTP-lesioned primates. MPTP-lesioned cynomolgus monkeys received acute oral administration of either vehicle or Formula (i) (1, 10 or 20 mg/kg) according to a randomized incomplete Latin Square-type. Dyskinesia was assessed every 10 min over the entire 6 h observation. Data are median values (FIG. 15A shows time-course) or median bars with individual animal scores (cumulated for 0-3 h shown in FIG. 15B or for 3-6 h shown in FIG. 15C). N=8 for all treatment groups. All zero values.
Figure 15:
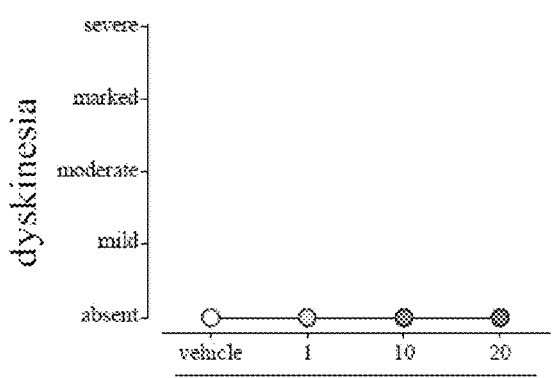
Figure 15:
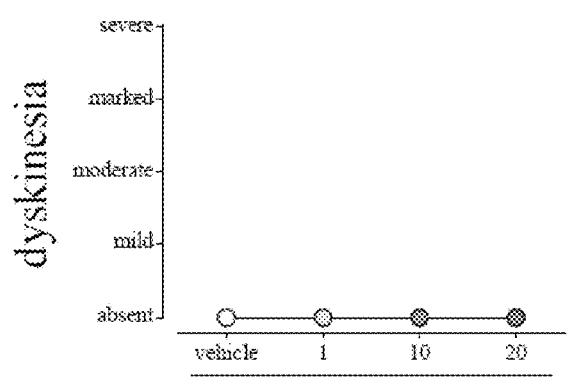

In L-DOPA naïve MPTP-lesioned macaques Formula (i) administration did not evoke dyskinesia at any of the doses assessed as shown in FIG. 15A. In L-DOPA naïve MPTP-lesioned macaques there was no dyskinesia evident following treatment with vehicle. Examining the whole 6 h time-course period of observation revealed no induction of dyskinesia in response to Formula (i) treatment at any time-point. As all values were zero no statistical analyses were undertaken (FIGS. 15 A-C). This is also true for the results shown in FIG. 16.

Example 3

Behavioral Effect of Acute DPI-289 Administered in Combination with Low and High Dose of L-DOPA This study utilized female MPTP-lesioned cynomolgus macaques that have received chronic repeat-treatment with L-DOPA and manifested stable and reproducible dyskinesia, of choreic and dystonic nature, in response to subsequent L-DOPA-treatments. Eight cynomolgus monkeys (*Macaca fascicularis,* 7.6-13.1 years of age, 3.0-4.5 kg) were used in this study. In a prior experiment, for each individual animal a low and high dose of L-DOPA was established such that the low dose (LD1) provided modest anti-parkinsonian action (1-2 h) and elicited predominantly non-disabling dyskinesia, the high dose (LDh) provided the best anti-parkinsonian effect achievable but also elicited disabling dyskinesia and an anti-parkinsonian benefit of 2-3 h duration The behavioral effects of acute DPI-289 administered in combination with low-dose L-DOPA (LD1) were assessed. Also higher dose of L-DOPA was also assessed without the addition of DPI-289. The low dose (LD1) was about 10 to 11 mg/kg of L-DOPA which is considered to be sub-optimal in terms of anti-parkinsonian benefit. The dose of DPI-289 was 20 mg/kg and the high dose of L-DOPA was about 30 to 31 mg/kg and considered to an optimal does in terms of anti-parkinsonian benefit but with disabling dyskinesia. The DPI-289 was administered one (1) hour prior to the L-DOPA and start of observation. Activity counts were collected and parkinsonian disability and dyskinesia was assessed via post-hoc analysis of video-recordings by a movement disorder neurologist blinded to treatment.

On the day before behavioral observations, food was removed overnight, from 5 p.m. On days of behavioral assessment, treatment was administered to the animals in their home cage at approximately 9 a.m. A 6 h period of observation then commenced 1 h after oral dosing.

The animals were rendered parkinsonian by once daily subcutaneous injection of 0.2 mg/kg MPTP, administered for 8-12 days, until the first appearance of parkinsonism symptoms. After this time, a parkinsonian syndrome reached a moderate to marked level, over approximately 30 days, and stabilized. Additional administrations of MPTP were given to some animals to titrate to similar degrees of parkinsonism in individuals across the group. The monkeys were allowed to recover for a minimum of further 30 days until their parkinsonism was demonstrated as being stable. Sixty days after commencing MPTP administration, L-DOPA (25 mg/kg) was administered orally twice daily for at least two months. L-DOPA was given with the decarboxylase inhibitor benserazide (as Madopar™). This treatment leads to the development of motor fluctuations, including dyskinesia.

Figure 17:
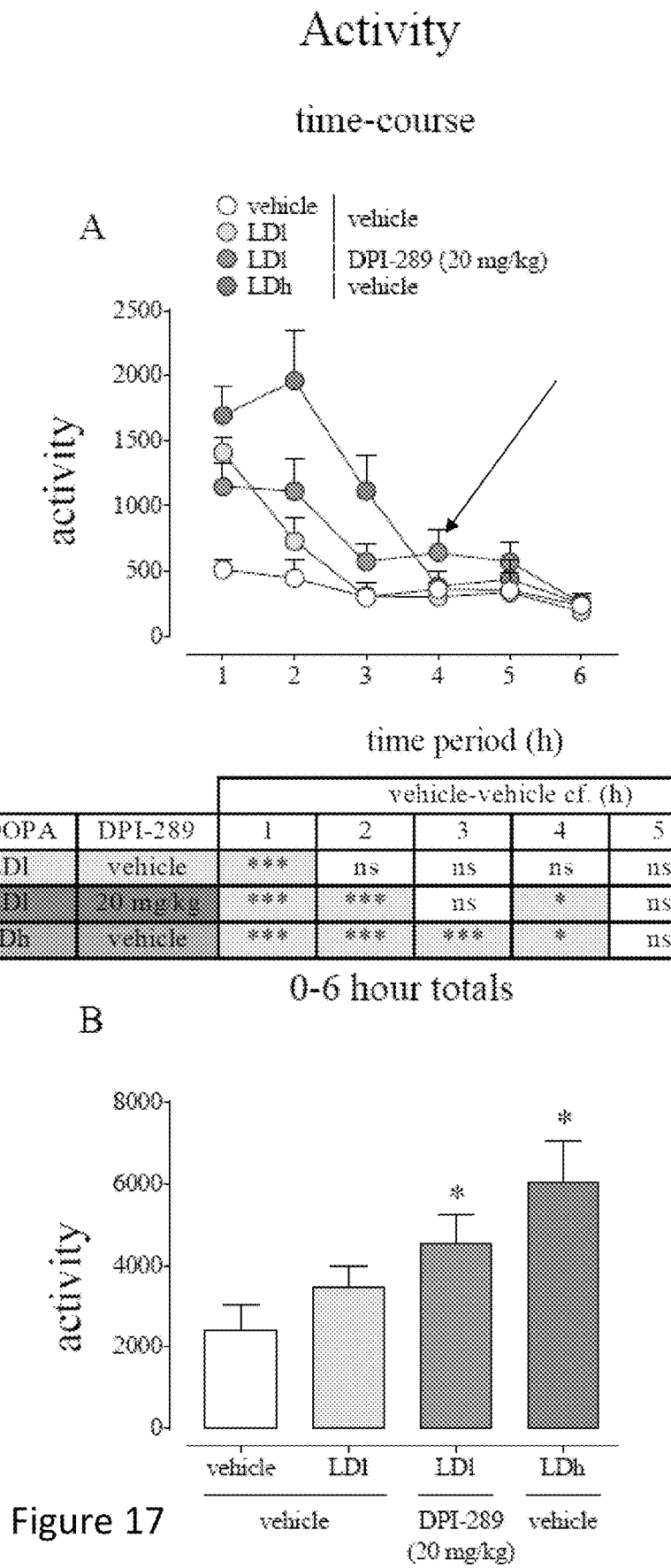
FIG. 17 shows the motor activity effect of acute DPI-289 administered in combination with low and high dose of L-DOPA in macaques with established motor complications due to administered L-DOPA. The dose of L-DOPA was individualized to each animal, the low dose being sub-therapeutic but which caused minimal dyskinesia and the high dose being a therapeutic but which also caused disabling dyskinesia. This activity is measured by an infra-red movement detector and captures all movement, normal and abnormal. Data are mean±s.e.m.

FIG. 17 shows that the synergistic combination of DPI-289 at 20 mg/kg in combination with low-dose of L-DOPA provided for extended activity into four and five hours (arrow) and beyond the use of the high dose of L-DOPA.

Figure 18:
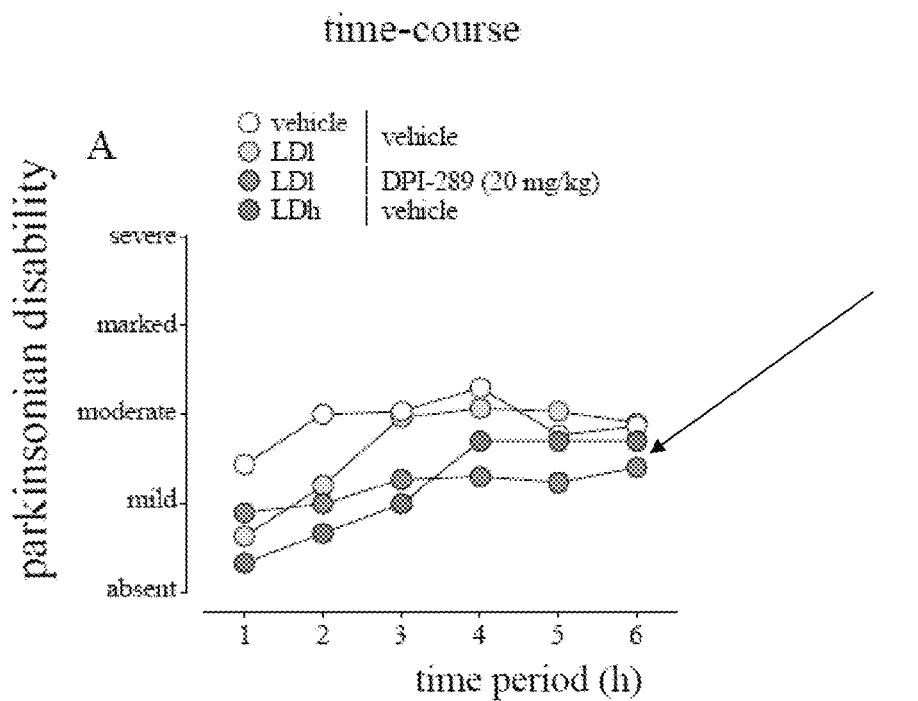
FIG. 18 shows the parkinsonian disability effect of acute DPI-289 administered in combination with low and high dose of L-DOPA. Parkinsonian disability is scored by a trained neurologist who is blinded to treatment allocation but is trained to differentiate normal from abnormal movements and is able to distinguish diminution of Parkinsonian disability from dyskinetic (abnormal) movements. Data are mean±s.e.m.
Figure 18:
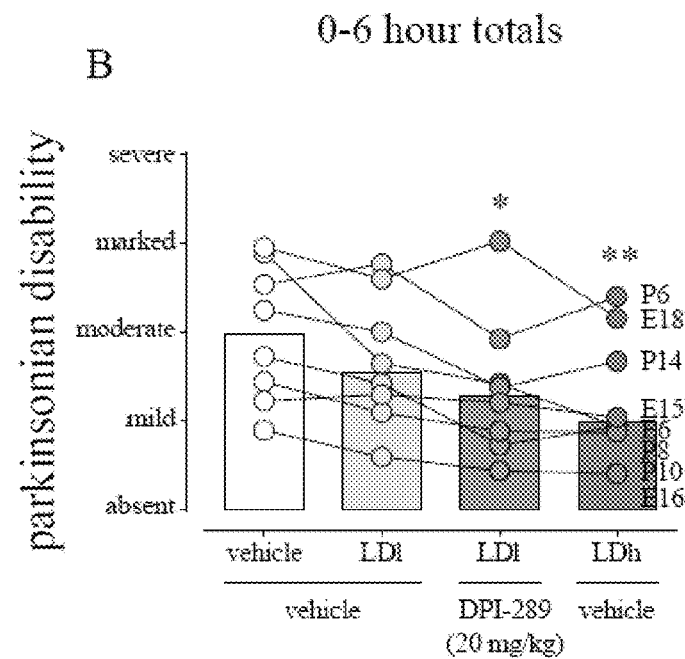

FIG. 18 shows that the synergistic combination of DPI-289 at 20 mg/kg in combination with low-dose of L-DOPA provided for an even and consistent level of fairly mild parkinsonian disability and as viewing the results in FIG. 18A, it is evident that with higher doses of L-DOPA the parkinsonian disability increased in the last four to six hours. The synergistic combination provides the most consistent results as shown by the arrow, wherein the combination of sub-therapeutic L-DOPA in combination with DPI-289 lasted at least 6 hours.

Figure 16:
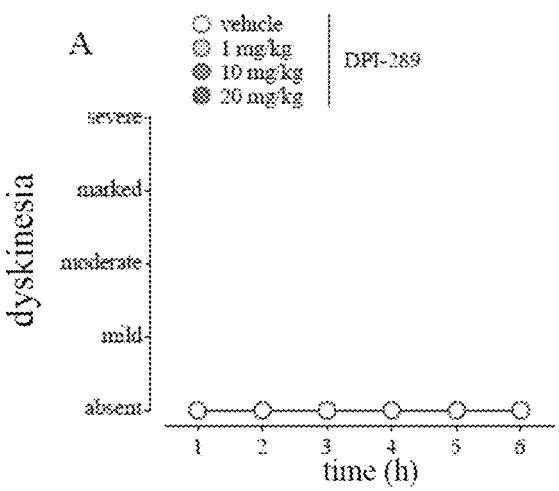
FIG. 16 shows the results of administration of DPI-289 in MPTP treated macaques with established motor complications due to administered L-DOPA. Data are mean±s.e.m.
Figure 16:
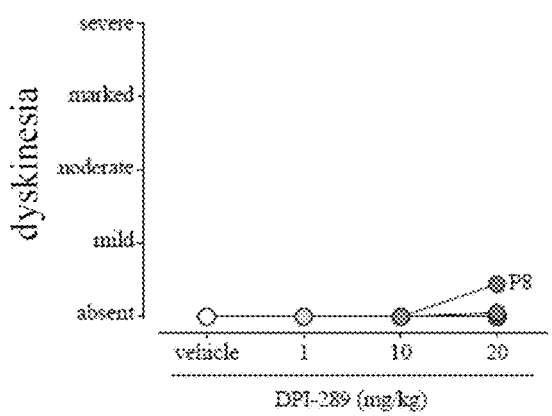
Figure 16:
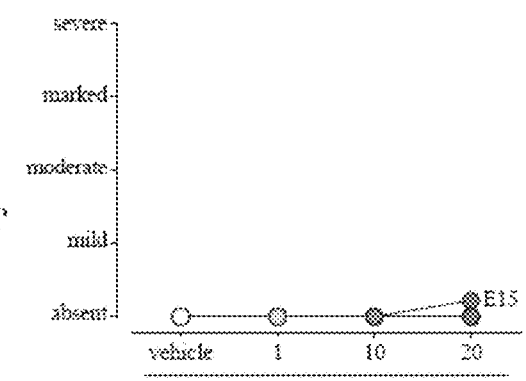
Figure 19:
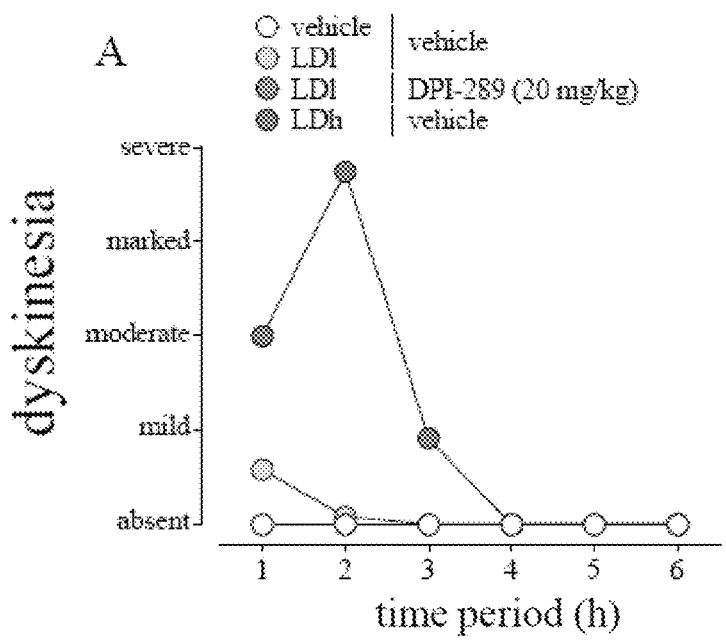
FIG. 19 shows the level of dyskinesia effect of acute DPI-289 administered in combination with low and high dose of L-DOPA in the same animals as displayed in FIGS. 17 & 18. Data are mean±s.e.m.
Figure 19:
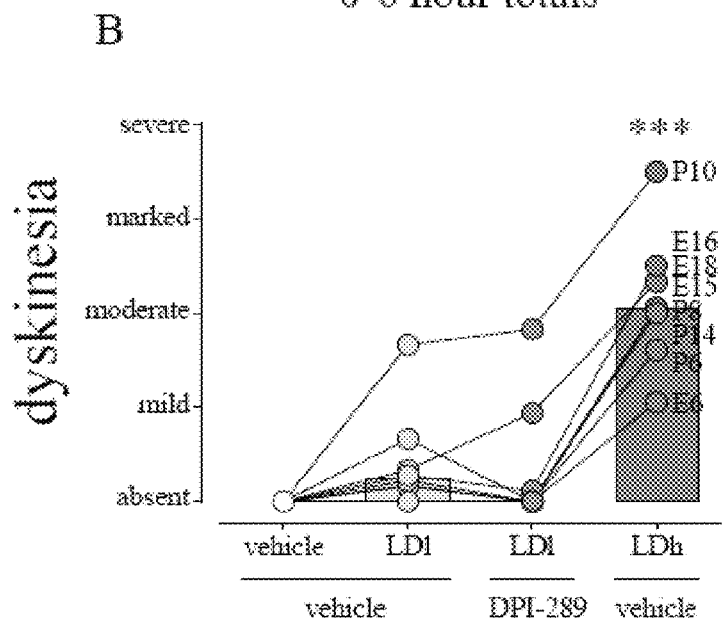

FIG. 19 shows that the synergistic combination of DPI-289 at 20 mg/kg in combination with low-dose of L-DOPA provided no additional dyskinesia to that exhibited by low-dose L-DOPA alone while the high dose of L-DOPA exhibited severe dyskinesia in the first three hours after dosage. The figure shows that augmentation effect of DPI was not associated with any increase in Dyskinesia. It is evident that the therapeutic dose of L-DOPA causes significant dyskinesia which last the duration of the therapeutic effect. In sharp contrast addition of Dpi 289 which augmented the effect of sub-therapeutic doses of L-DOPA did not result in any increased dyskinesia. FIGS. 15 & 16 demonstrated that DPI-289 does not cause dyskinesia in neither L-DOPA naïve nor in L-DOPA primed animals. This data shows that DPI-289 does not increase L-DOPA induced dyskinesia and may even lower it. It is theorized that DPI-289 having both delta opioid agonist activity and mu opioid antagonist activity eliminates or greatly reduces dyskinesia activity.

Figure 20:
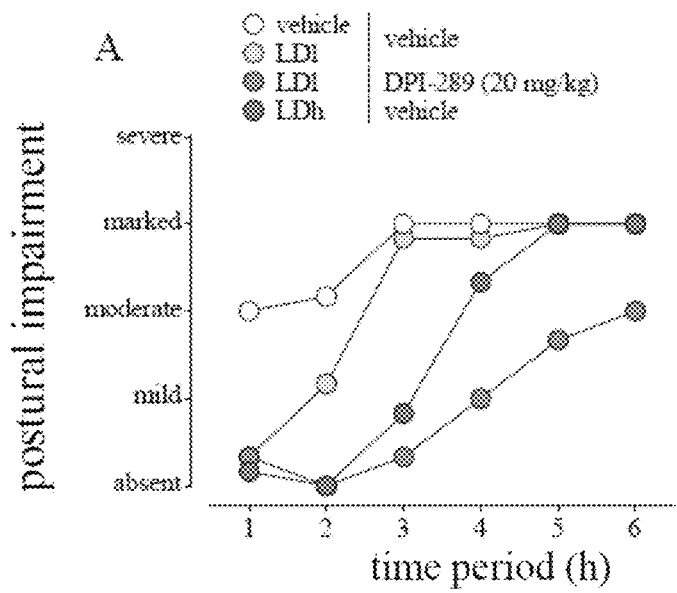
FIG. 20 shows the postural instability effect of acute DPI-289 administered in combination with low and high dose of L-DOPA in the same animals as displayed in FIGS. 17 & 18. Data are mean±s.e.m.
Figure 20:
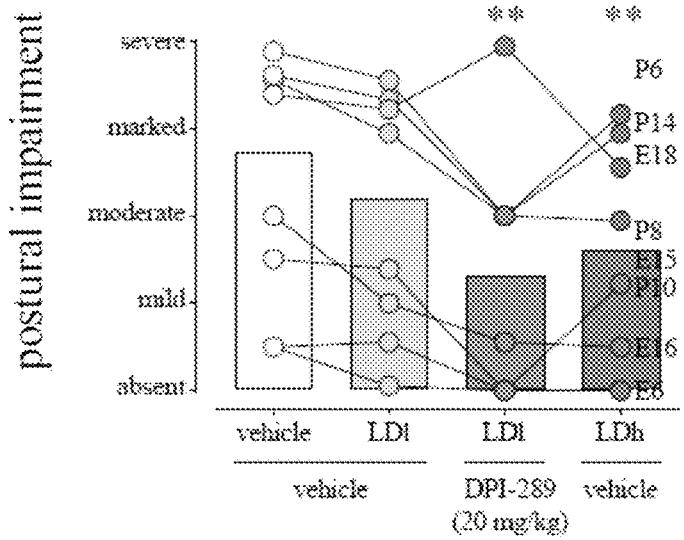

FIG. 20A shows that the synergistic combination of DPI-289 at 20 mg/kg in combination with low-dose of L-DOPA provided for reduced postural instability from about 2 to 6 hours after the dosing and clearly the synergistic combination showed that such a combination was more effective than the high dose of L-DOPA or DPI-289 alone as shown in FIG. 12.

Figure 21:
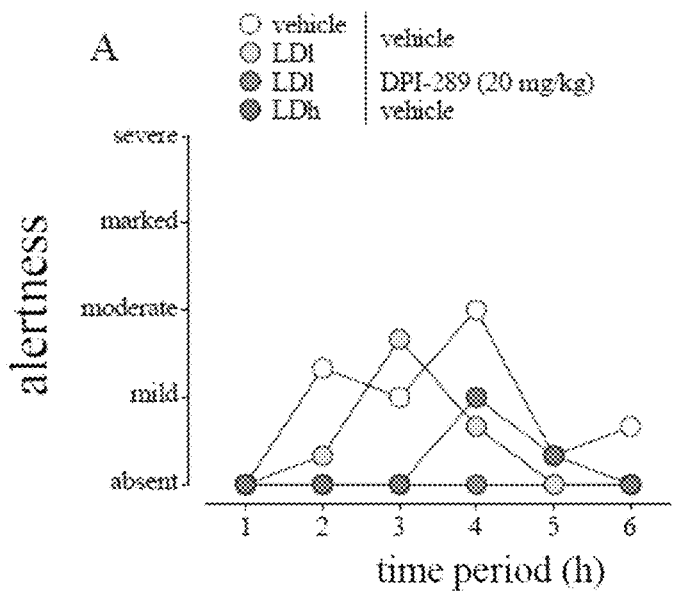
FIG. 21 shows the alertness effect of acute DPI-289 administered in combination with low and high dose of L-DOPA in the same animals as displayed in FIGS. 17 & 18. Data are mean±s.e.m.
Figure 21:
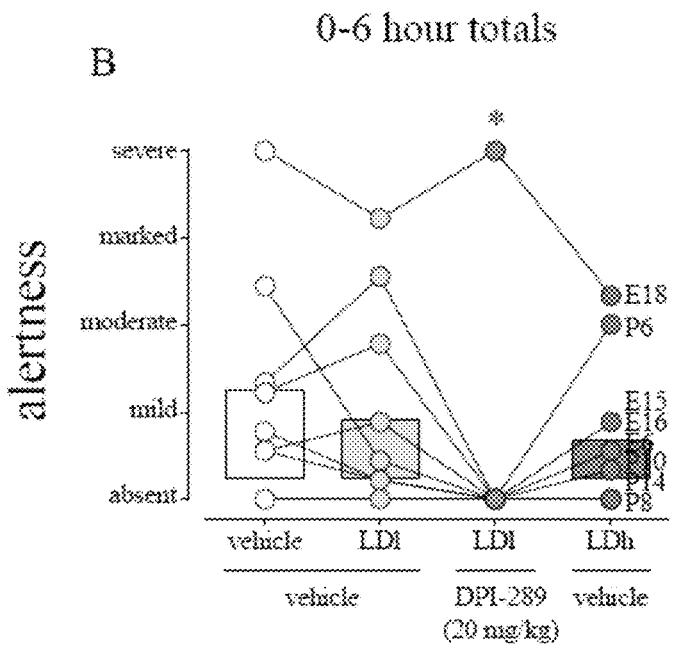

FIG. 21 shows that the synergistic combination of DPI-289 at 20 mg/kg in combination with low-dose of L-DOPA provided for an improvement in alertness value that mirrored that of the high dose of L-DOPA and importantly the beneficial effects actually lasted longer than for high dose L-DOPA alone.

Figure 22:
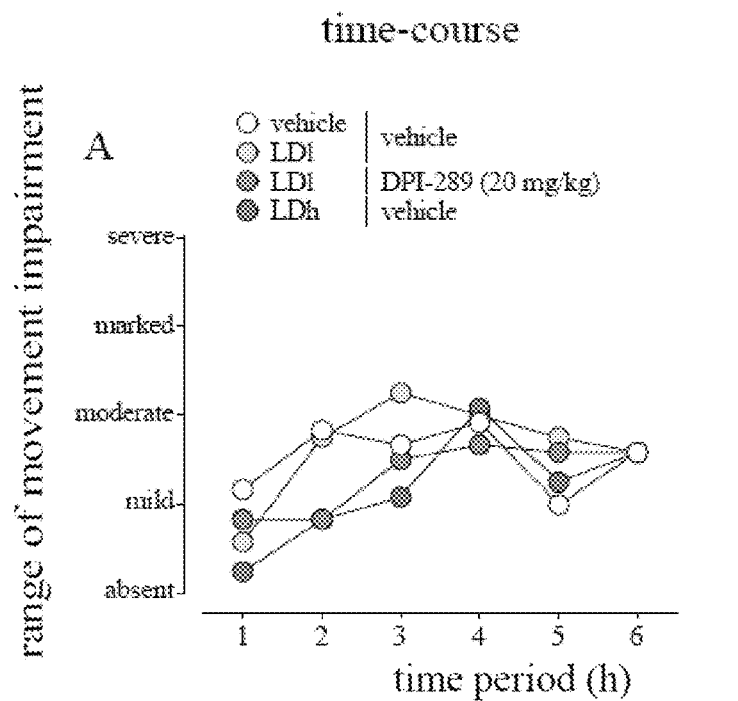
FIG. 22 shows the range of movement impairment effect of acute DPI-289 administered in combination with low and high dose of L-DOPA in the same animals as displayed in FIGS. 17 & 18. Data are mean±s.e.m.
Figure 22:
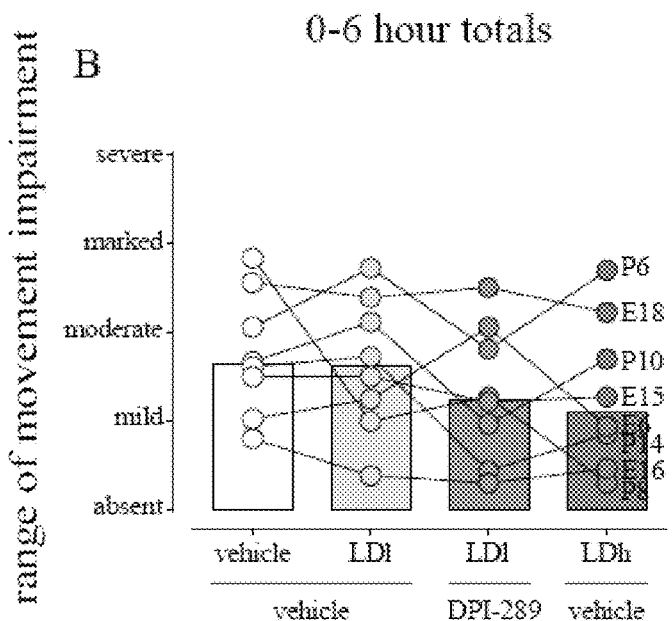

FIG. 22 shows that the synergistic combination of DPI-289 at 20 mg/kg in combination with low-dose of L-DOPA provided for reduced range of movement impairment than low dose L-DOPA alone but this difference did not reach statistical significance. It would appear that the combination therapy resulted in more consistent reduction in range of movement impairment than low or high dose L-DOPA alone.

Figure 23:
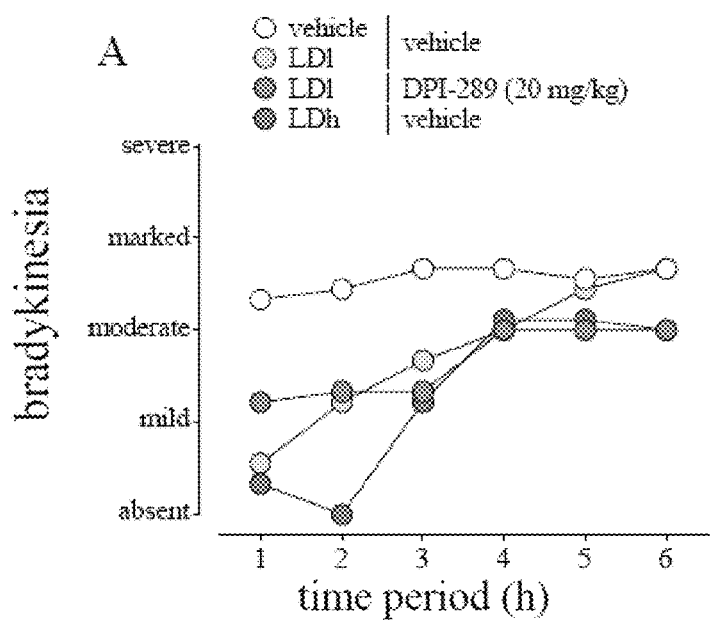
FIG. 23 shows the bradykinesia effect of acute DPI-289 administered in combination with low and high dose of L-DOPA in the same animals as displayed in FIGS. 17 & 18. Data are mean±s.e.m.
Figure 23:
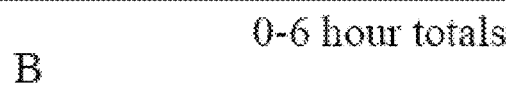

FIG. 23 shows that the synergistic combination of DPI-289 at 20 mg/kg in combination with low-dose of L-DOPA provided for the same level of bradykinesia as that of the high dose of L-DOPA for the hours of three to six hours after dosing. Further for the first three hours showed less bradykinesia from that shown in FIG. 8. Again, as seen in FIG.

22, it would appear that the combination therapy resulted in more consistent levels of bradykinesia than low or high dose L-DOPA alone (arrow).

Figure 24:
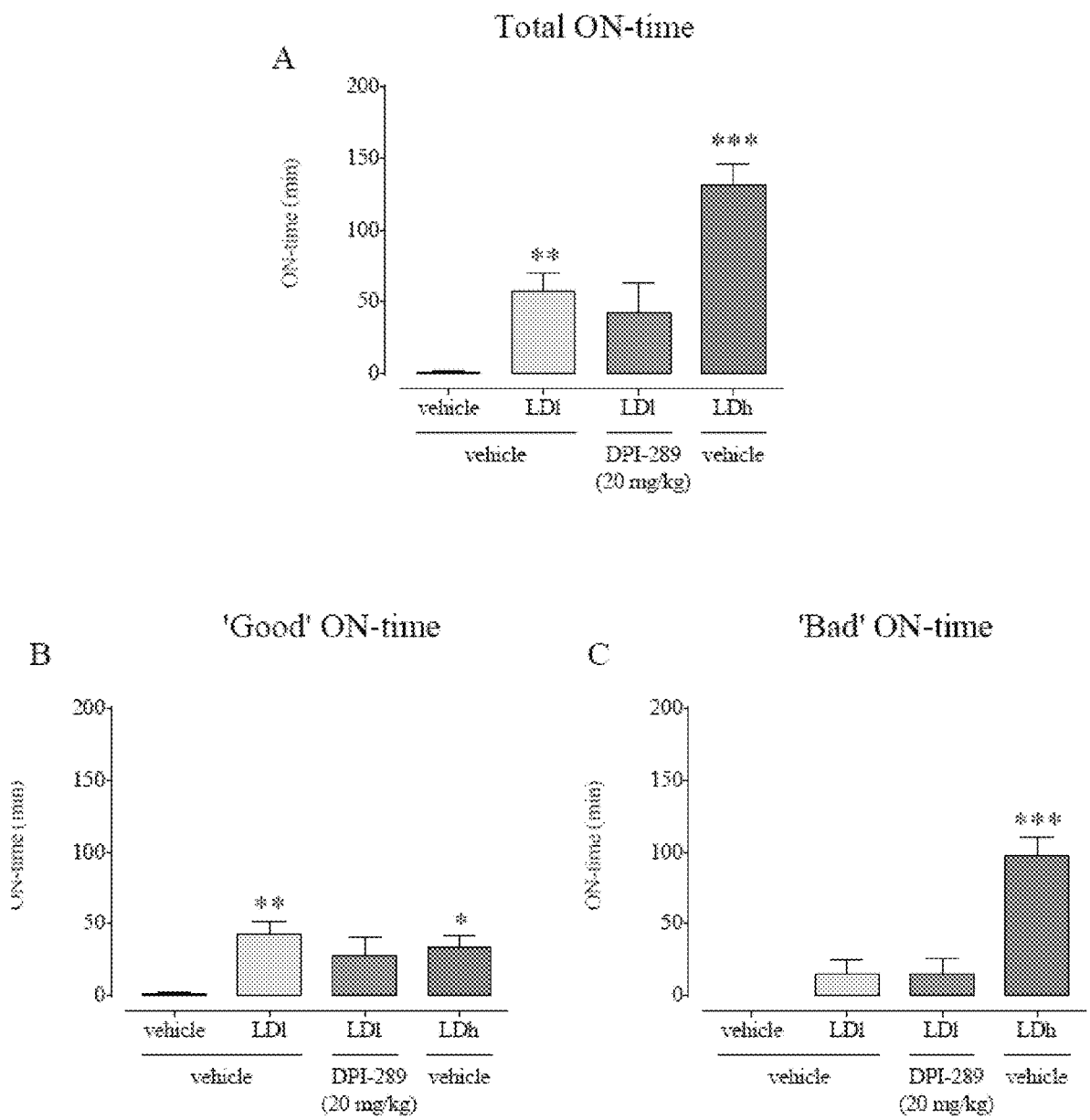
FIG. 24 shows the total ON-time effect of acute DPI-289 administered in combination with low and high dose of L-DOPA.

FIG. 24 shows that the synergistic combination of DPI-289 at 20 mg/kg in combination with low-dose of L-DOPA provided for comparable 'good' time as that of the high dose of L-DOPA and considerably less of 'bad' time (ON-time with disabling dyskinesia) relative to the high dose of L-DOPA and certainly an increase in good on-time relative to the results shown in FIG. 4.

Example 4

Rodent Model of PD Showed the Use of DPI-289 Increased Locomotor Activity without Causing Dyskinesia.

Figure 25:
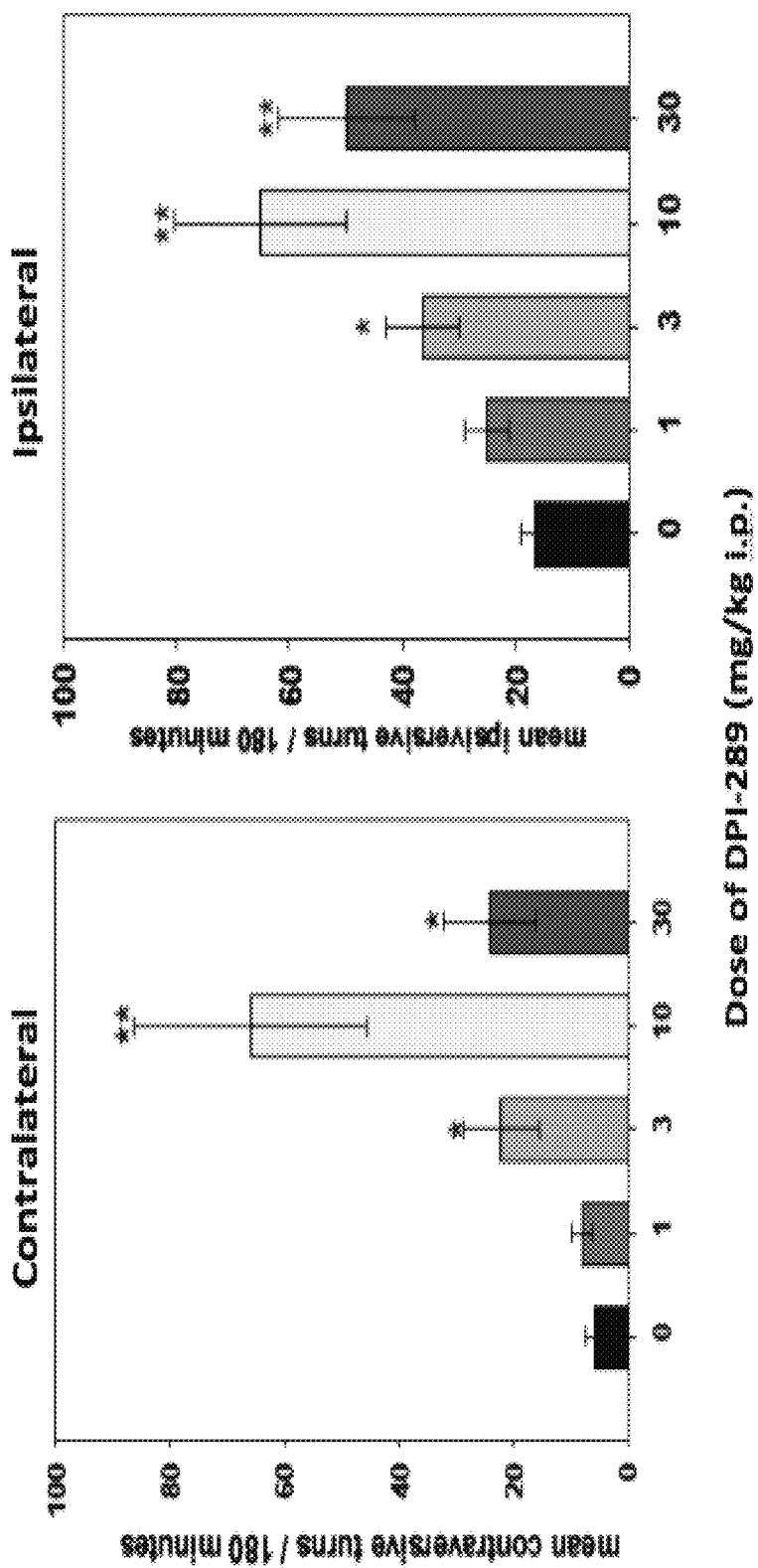
FIG. 25 shows the increase in contralateral and ipsilateral rotations by DPI-289 in 6-OHDA-lesioned rats. N=6 rats per group, Newman-Keuls post hoc test was used for statistical significance.
Figure 26:
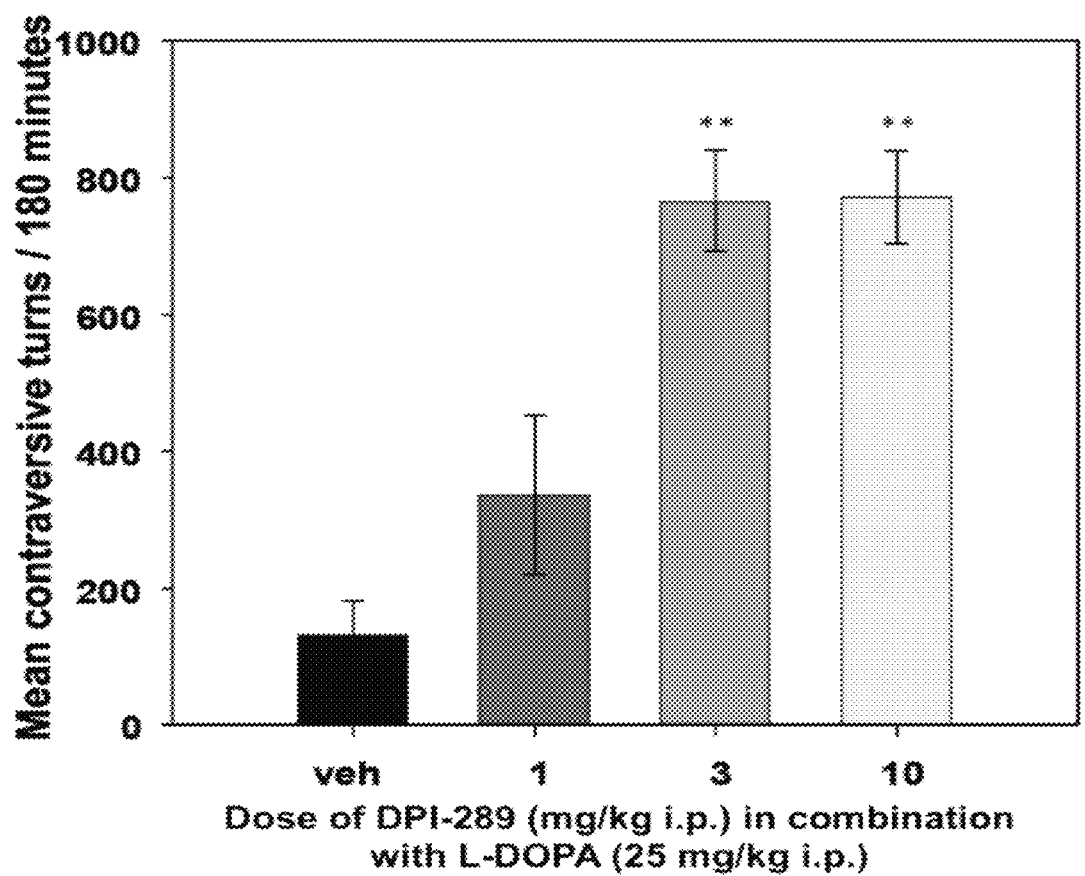
FIG. 26 shows augmentation of L-DOPA-induced contralateral rotations by coadministration of DPI-289 in 6-OHDA-lesioned Rats. N=8 per group, Newman-Keuls post hoc test for statistical significance.

In a rat model of PD, focal injection of the neurotoxin 6-hydroxydopamine (6-OHDA) was used to create a unilateral lesion of the nigrostriatal dopamine pathway. When challenged with dopamine agonists, rats rotate in the direction contralateral to the lesion and the number of rotations may be used as a measure of anti-parkinsonian efficacy. Administration of DPI-289 (1-10 mg/kg i.p.) caused a dose-related increase in both contralateral and ipsilateral rotations, a profile that suggests the effect is not mediated through dopaminergic mechanism; a higher dose of 30 mg/kg also increased rotations but the effect on contralateral rotations appeared to be diminished, possibly due to sedation at this dose as shone in FIG. 25. When co-administered with a sub-optimal dose of L-DOPA (25 mg/kg i.p.), DPI-289 caused a marked potentiation of contralateral rotations, suggesting that it has utility as an adjunct to augment the anti-parkinsonian activity of L-DOPA, as shown in FIG. 26.

Rats with unilateral 6-OHDA lesions also have motor incoordination when they are placed on a slowly rotating drum (rotarod). Daily administration of DPI-289 (3 mg/kg p.o.) or L-DOPA (6 mg/kg i.p.) for 15 days reduced or reversed the postural asymmetry and this was maintained throughout treatment duration as shown in FIG. 27A. Animals receiving L-DOPA developed abnormal involuntary movements (AIMs: dyskinesia) on the side of the body opposite the lesion, characterized by twisting of the neck and trunk, jerky movements of the forelimb and paw, and orofacial movements (chewing, tongue protrusion). Unlike L-DOPA, daily administration of DPI-289 for 15 days did not elicit dyskinesia in 6-OHDA-lesioned rats, shown in FIG. 27B. Notably, the erratic responses to L-DOPA, shown in FIG. 27A, were likely due to the dyskinetic movements interfering with the scoring for asymmetry.

While the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

REFERENCES

The contents of the following references are hereby incorporated by reference herein for all purposes.

Broom D C, Jutkiewicz E M, Folk J E, Traynor J R, Rice K C, Woods J H, (2002), Nonpeptidic delta-opioid receptor agonists reduce immobility in the forced swim assay in rats. *Neuropsychopharmacology* 26(6):744-755.

Chang K J, Rigdon G C, Howard J L and McNutt R W, (1993), A novel, potent and selective nonpeptidic delta opioid receptor agonist BW373U86. *J Pharmacol Exp Ther* 267(2):852-857.

Comer S D, Hoenicke E M, Sable A I, McNutt R W, Chang K J, De Costa B R, Mosberg H I and Woods J H (1993) Convulsive effects of systemic administration of the delta opioid agonist BW373U86 in mice. *J Pharmacol Exp Ther* 267(2):888-895.

Cuello C A, Paxinos G, (1978) Evidence for a long leu-enkephalin striopallidal pathway in rat brain. *Nature* 271:178-180

De Ceballos M L, Fernandez A, Jenner, Marsden C D, (1993) Parallel alterations in Met-enkephalin and substance P levels in medial globus pallidus in Parkinson's disease patients. *Neurosci. Lett.* 160:163-166

Gerfen C R, Young Ws 3$^{rd}$, (1988) Distribution of striatonigral and striatopallidal peptidergic neurons in both patch and matrix compartments: An in situ hybridization histochemistry and fluorescent retrograde tracing study. *Brain Res.* 460:161-167

Henry B, Brotchie J M, (1996) Potential of opioid antagonists in the treatment of levodopa-induced dyskinesias in Parkinson's disease. *Drugs Aging* 9:149-158

Henry B, Fox S H, Crossman A R, and Brotche, J M, (2001) Mu ☐ and delta-opioid receptor antagonist reduce levodopa-induced dyskinesia in the MPTP-lesioned primate model of Parkinson's disease. *Experimental Neurology* 171:139-146

Hill M P, Hille C J, Brotchie J M, (2000) δ opioid receptor agonists as a therapeutic approach in Parkinson's disease. *Drugs News Perspect.* 13(5):261-268

Hille C J, Fox S H, Maneuf Y P, Crossman A R, Brotchie J M, (2001) Antiparkinsonian action of a δ opioid agonist in rodent and primate models of Parkinson's disease. *Exp. Neurol.* 172:189-198

Herrero M T, Augood S J, Hirsch E C, Javoy-Agid F, Luquin M R, Agid Y, Obeso J A, Emson P C, (1995) Effects of L-DOPA on preproenkephalin and preprotachykinin gene expression in MPTP-treated monkey striatum. *Neurosci.* 68:1189-1198

Jolkkonen J, Jenner O, Marsden C D, (1995) L-DOPA reverses altered gene expression of substance P but not enkephalin in the caudate-putamen of common marmosets treated with MPTP. *Brain Res. Mol. Brain Res.* 32:297-307

Maneuf Y P, Mitchell I J, Crossman A R, Brotchie J M, (1994) On the role of enkephalin cotransmission in the GABAergic striatal efferents to the globus pallidus. *Exp. Neurol.* 125:65-71

Negus S S, Gatch M B, Mello N K, Zhang X, Rice K (1998) Behavioral effects of the delta-selective opioid agonist SNC80 and related compounds in rhesus monkeys. *J. Pharmacol. Exp. Ther.,* 286: 362-75

Negus S S, Mello N K, Portoghese P S, Lukas S E, Mendelson J H, (1995) Role of delta opioid receptors in the reinforcing and discriminative stimulus effects of cocaine in rhesus monkeys. *J. Pharmacol. Exp. Ther.,* 273: 1245-56

Negus S S, Butelman E R, Chang K-J, DeCosta B, Winger G, Woods J H, (1994) Behavioral effects of the systemically active delta opioid agonist BW373U86 in rhesus monkeys. *J Pharmacol. Exp. Ther.,* 270, 1025-34

Nisbet A P, Foster O J, Kingsbury A, Eve D J, Daniel S E, Marsden C D, Lees A J, (1995) Perproenkephalin and preprotachykinin messenger RNA expression in normal human basal ganglia and in Parkinson's disease. *Neurosci.* 66:361-376

Silverdale M A, Fox S H, Crossman A R, Brotchie J M, (2003) Potential nondopaminergic drugs for Parkinson's disease. *Parkinson's Disease: Advances in Neurology* 91:273-291

That which is claimed:

1. A method of treatment for a patient/subject who is L-DOPA experienced and having L-DOPA induced dyskinesia adverse events selected from over activity of movement, dyskinesia, postural instability and/or reduced alertness, wherein the treatment comprises administering a combination consisting of a therapeutically effective amount of formula (i):

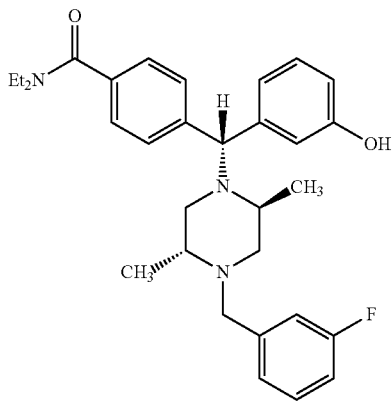

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt in combination with a lower dose of L-DOPA to a subject in need of such treatment, wherein the compound of formula (i) is in a dose of about 20 mg/kg and wherein the sub-optimal and low dose of L-DOPA is about 10 mg/kg.

2. An L-DOPA sparing method of treatment for a subject with Parkinson's disease in a patient who is benefiting from L-DOPA treatment but suffering from L-DOPA induced dyskinesia resulting in hyperkinetic movements, selected from the group consisting of chorea, dystonia, and athetosis adverse events, wherein the treatment comprises of reducing the L-DOPA dose to a sub-optimal and low dose to reduce the L-DOPA induced dyskinesia and administering a therapeutically effective amount of formula (i):

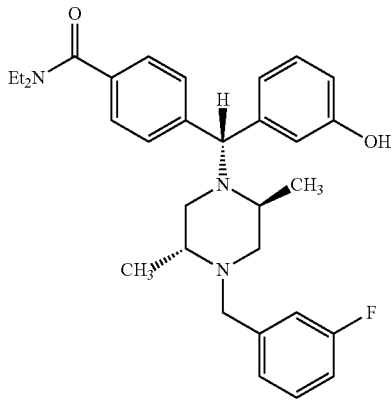

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt thereof to a subject in need of such treatment, wherein the compound of formula (i) is in a dose of about 20 mg/kg per day to maintain or achieve an antiparkinsonian effect despite reduction of the L-DOPA dose, wherein the sub-optimal and low dose of L-DOPA of about 20 mg/kg.

3. A composition comprising a synergistic combination of L-DOPA in an amount of about 10 mg/kg and formula (i) (DPI-289)

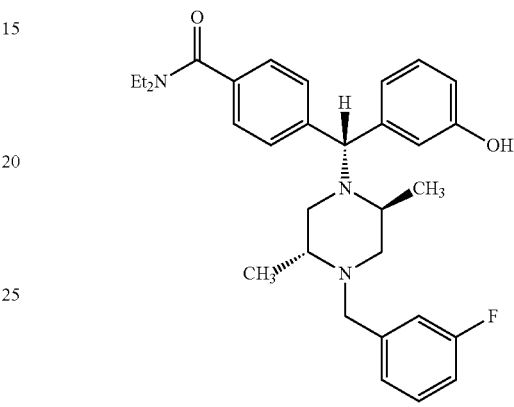

4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt thereof in an amount, of about 20 mg/kg where that combination causes a synergistic effect that provides for extended reduction in Parkinsonian symptoms relative to either components alone or a higher dose of L-DOPA alone.

4. A method of reducing L-DOPA induced dyskinesia in patients with Parkinson's Disease by administering a combination consisting of the following compound formula (i)

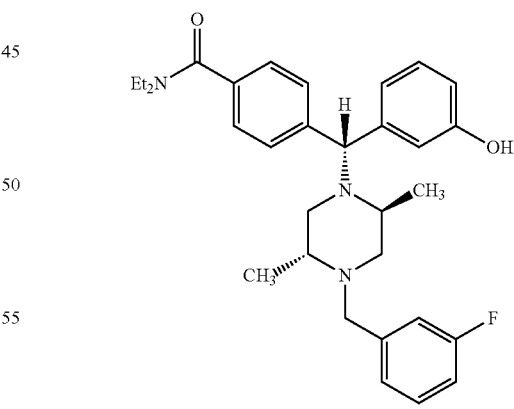

or a pharmaceutically acceptable salt thereof, wherein the compound formula (i) is administered to a subject in need of treatment in a dose of 20 mg/kg in combination with L-DOPA, wherein the L-DOPA is in a sub-optimal and low dose is about 10 mg/kg.

5. A combination of compounds consisting of L-DOPA in an amount of about 10 mg/kg and formula (i) (DPI-289)

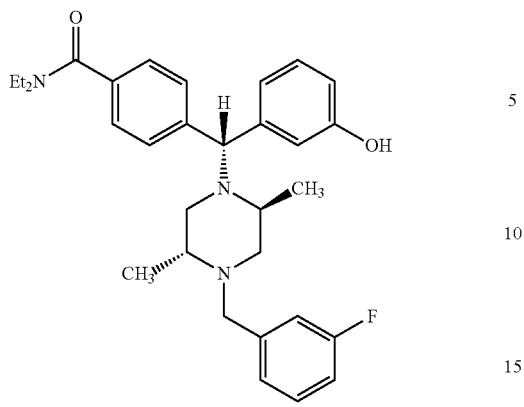
4-((alpha-R)-alpha-((2S,5R)-2,5-Dimethyl-4-(3-fluorobenzyl)-1-piperazinyl)-3-hydroxybenzyl)-N,N-diethylbenzamide or a pharmaceutically acceptable salt thereof in an amount of about 20 mg/kg where that combination causes a therapeutic effect that provides for extended reduction in Parkinsonian symptoms relative to either components alone or a higher dose of L-DOPA alone.
* * * * *